United States Patent [19]

Roberts et al.

[11] Patent Number: 5,236,936
[45] Date of Patent: Aug. 17, 1993

[54] PYRIDINE COMPOUNDS WHICH ARE USEFUL AS ANGIOTENSIN II RECEPTOR ANTAGONISTS

[75] Inventors: David A. Roberts, Congleton; Robert H. Bradbury, Wilmslow; Martin P. Edwards, Rollington; Arnold H. Ratcliffe, Poynton, all of England

[73] Assignee: Imperial Chemical Industries PLC, London, England

[21] Appl. No.: 834,037

[22] Filed: Feb. 11, 1992

[30] Foreign Application Priority Data

Feb. 11, 1991 [GB] United Kingdom ............... 9102803

[51] Int. Cl.$^5$ ............... C07D 401/12; A61K 31/44
[52] U.S. Cl. ............... 514/340; 514/350; 546/298
[58] Field of Search ............... 546/276, 208; 514/340, 514/350

[56] References Cited

U.S. PATENT DOCUMENTS

| | | | |
|---|---|---|---|
| 4,820,843 | 4/1989 | Aldrich et al. | 548/252 |
| 4,880,804 | 11/1989 | Carini et al. | 514/234.5 |

FOREIGN PATENT DOCUMENTS

| | | | |
|---|---|---|---|
| 0253310 | 1/1988 | European Pat. Off. | 548/252 |
| 0323841 | 7/1989 | European Pat. Off. | 548/252 |
| 0412848 | 2/1991 | European Pat. Off. | 546/212 |
| 0453210 | 4/1991 | European Pat. Off. | 546/276 |
| 0445811 | 9/1991 | European Pat. Off. | 546/330 |
| 0475206 | 3/1992 | European Pat. Off. | 544/123 |
| 0487745 | 6/1992 | European Pat. Off. | 546/276 |
| 0008201 | 6/1991 | France | 546/276 |

OTHER PUBLICATIONS

G. R. Proctor, et al., "Azabenzocycloheptenones. Part XIV. Cyclisation of Amino-acid Derivatives to Tetrahydro-1-benzazepin-5-ones and Tetrahydroquiolin-4-ones", *J. Chem. Soc., Perkin Trans. I* (1972), 1803–08.

*Primary Examiner*—C. Warren Ivy
*Assistant Examiner*—Zinna N. Davis
*Attorney, Agent, or Firm*—Thomas E. Jackson

[57] ABSTRACT

The invention concerns pharmaceutically useful compounds of the formula I, in which $R^1$, $R^2$, $R^3$, $R^4$, $R^5$, $R^6$, $R^7$, X and Z have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

9 Claims, No Drawings

PYRIDINE COMPOUNDS WHICH ARE USEFUL AS ANGIOTENSIN II RECEPTOR ANTAGONISTS

This invention concerns novel pyridine compounds and, more particularly, novel pyridine compounds which possess pharmacologically useful properties in antagonising at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

In European Patent Application, Publication No. 453210 there is described certain pyridine derivatives having angiotensin II inhibitory properties.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a pyridine compound of the formula I (set out hereinafter, together with the other chemical formulae identified by Roman numerals) wherein $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, (1-4C)alkoxy or phenyl substituent; $R^2$ is hydrogen, (1-8C)alkyl, (3-8C)cycloalkyl, (3-8C)cycloalkyl-(1-4C)alkyl, carboxy, (1-4C)alkoxycarbonyl, (3-6C)alkenyloxycarbonyl, cyano, nitro, phenyl or phenyl(1-4C)alkyl; $R^3$ is selected from halogeno, (1-4C)alkoxy, amino, alkylamino and dialkylamino of up to 6 carbon atoms, and any of the values defined for $R^1$; $R^4$ is a benzoyl group, the phenyl group of which is unsubstituted or bears one or two substituents independently selected from (1-4C)alkyl, (1-4C)alkoxy, halogeno, cyano, trifluoromethyl, nitro, hydroxy, carboxy, (1-4C)alkanoylamino, (1-4C)alkanoyl, fluoro(1-4C)alkoxy, hydroxy(1-4C)alkyl, (1-4C)alkoxy(1-4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1-4C)alkoxycarbonyl, (1-4C)alkanesulphonamido, (1-4C)alkyl.S(O)$_n$-[in which n is zero, 1 or 2], 1H-tetrazol-5-yl, phenyl, phenoxy, benzyloxy, benzyloxycarbonyl, benzamido and benzenesulphonamido, the benzene moiety of the last six groups optionally bearing a halogeno, (1-4C)alkyl or (1-4C)alkoxy substituent; or $R^4$ is a phenyl or phenyl(1-4C)alkyl group, wherein the phenyl ring of which last two groups bears one or two substituents independently selected from nitro, hydroxy, carboxy, (1-4C)alkanoylamino, (1-4C)alkanoyl, fluoro(1-4C)alkoxy, hydroxy(1-4C)alkyl, (1-4C)alkoxy(1-4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1-4C)alkoxycarbonyl, (1-4C)alkanesulphonamido, (1-4C)alkyl.-S(O)$_n$-[in which n is zero, 1 or 2], 1H-tetrazol-5-yl, phenyl, phenoxy, benzyloxy, benzyloxycarbonyl, benzamido and benzenesulphonamido, the benzene moiety of the last six groups optionally bearing a halogeno, (1-4C)alkyl or (1-4C)alkoxy substituent, and wherein when $R^4$ is a disubstituted phenyl or phenyl(1-4C)alkyl group one of the substituents may additionally be selected from (1-4C)alkyl, (1-4C)alkoxy, halogeno, cyano and trifluoromethyl; or $R^4$ is a group of the formula —$A^1.B^1$ wherein $A^1$ is (1-6C)alkylene, a carbonyl group or a direct bond and $B^1$ is a 5 or 6-membered saturated or unsaturated heterocyclic ring containing a single heteroatom selected from oxygen, sulphur and nitrogen or containing two heteroatoms one of which is nitrogen and the other is oxygen, sulphur or nitrogen, and wherein $B^1$ optionally bears a (1-4C)alkyl or (1-4C)alkoxy substituent; $R^5$ is hydrogen; $R^6$ is hydrogen or (1-4C)alkyl; $R^7$ is selected from hydrogen, (1-4C)alkyl, (1-4C)alkoxy, halogeno, trifluromethyl, cyano and nitro; X is phenylene optionally bearing a substituent selected from (1-4C)alkyl, (1-4C)alkoxy, halogeno, trifluoromethyl, cyano and nitro, or X is a direct bond between the adjacent phenyl group and the carbon atom bearing $R^5$ and $R^6$; Z is 1H-tetrazol-5-yl, —CO.NH.(1H-tetrazol-5-yl) or a group of the formula —CO.OR$^8$ or —CO.NH.SO$_2$.R$^9$ in which $R^8$ is hydrogen or a non-toxic, biodegradable residue of a physiologically acceptable alcohol or phenol, and $R^9$ is (1-6C)alkyl, (3-8C)cycloalkyl or phenyl; and wherein any of said phenyl moieties of $R^1$, $R^2$, $R^3$ or $R^9$ may be unsubstituted or bear one or two substituents independently selected from (1-4C)alkyl, (1-4C)alkoxy, halogeno, cyano and trifluoromethyl; or an N-oxide thereof; or a non-toxic salt thereof.

It will be appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$, $R^2$ or $R^3$ when it is alkyl is, for example, methyl, ethyl, propyl, butyl, isobutyl, sec-butyl, pentyl or hexyl; and when it is cycloalkyl is, for example, cyclopropyl, cyclopentyl or cyclohexyl.

A particular value for $R^1$ or $R^3$ when it is alkyl bearing one or more fluoro substitutents is, for example, fluoromethyl, trifluoromethyl, 2,2,2-trifluoroethyl or pentafluoroethyl; and when it is alkyl bearing a cycloalkyl, (1–4C)alkoxy or phenyl substituent is, for example, cyclopropylmethyl, cyclopentylmethyl, cyclohexylmethyl, 2-methoxyethyl, 2-ethoxyethyl, benzyl, 1-phenylethyl or 2-phenylethyl.

A particular value for $R^2$ when it is cycloalkyl-alkyl is, for example, cyclopropylmethyl, cyclopentylmethyl, cyclohexylmethyl or 2-cyclopentyl-ethyl; and when it is phenylalkyl is, for example, benzyl, 1-phenylethyl or 2-phenylethyl.

A particular value for $R^2$ when it is alkoxycarbonyl is, for example, methoxycarbonyl, ethoxycarbonyl or propoxycarbonyl; and when it is alkenyloxycarbonyl is, for example, allyloxycarbonyl, 2-methyl-2-propenyloxycarbonyl or 3-methyl-3-butenyloxycarbonyl.

A particular value for $R^6$ or $R^7$, or for an optional substituent which may be present when X is phenylene, when it is alkyl is, for example, methyl or ethyl.

A particular value for $R^3$, $R^7$ or for an optional substituent which may be present when X is phenylene, include, by way of example, for halogeno: fluoro, chloro, bromo and iodo; and for alkoxy: methoxy and ethoxy.

A particular value for $R^3$ when it is alkylamino is, for example, methylamino, ethylamino or butylamino; and when it is dialkylamino is, for example, dimethylamino, diethylamino or dipropylamino.

A particular value for $R^4$ when it is phenylalkyl is, for example, benzyl, 1-phenylethyl or 2-phenylethyl.

Particular values for a substituent on $R^4$ when it is phenyl or phenyl(1–4C)alkyl, or for an optional substituent on $R^4$ when it is benzoyl include, by way of example, for alkyl: methyl and ethyl; for alkoxy: methoxy and ethoxy; and for halogeno: chloro, bromo and iodo; for alkanoylamino: formamido, acetamido and propanamido; for alkanoyl: formyl, acetyl and butyryl; for fluoroalkoxy: trifluoromethoxy, 2-fluoroethoxy, 2,2,2-trifluoroethoxy and 3,3,3-trifluoropropoxy; for hydroxyalkyl: hydroxymethyl, 1-hydroxyethyl and 2-hydroxyethyl; for alkoxyalkyl: 2-methoxyethyl and 2-ethoxyethyl; for N-alkylcarbamoyl: N-methyl and N-ethylcarbamoyl; for di(N-alkyl)carbamoyl: N,N-dimethylcarbamoyl and N,N-diethylcarbamoyl; for N-alkylsulphamoyl: N-methyl and N-ethylsulphamoyl; for di(N-alkylsulphamoyl: N,N-dimethylsulphamoyl and N,N-diethylsulphamoyl; for alkoxycarbonyl: methoxycarbonyl, ethoxycarbonyl and propoxycarbonyl; for alkanesulphonamido: methanesulphonamido and ethanesulphonamido; for alkylthio: methylthio and ethylthio; for alkylsulphinyl; methylsulphinyl and ethylsulphinyl; and for alkylsulphonyl: methylsulphonyl and ethylsulphonyl; and for phenyl, phenoxy, benzyloxy, benzyloxycarbonyl, benzamido and benzenesulphonamido optionally bearing a substituent: phenyl, phenoxy, benzyloxy, benzyloxycarbonyl, benzamido and benzenesulphonamido optionally bearing a fluoro, chloro, bromo, methyl, ethyl, methoxy or ethoxy substituent.

A particular value for $A^1$ when it is alkylene includes, for example, methylene, ethylene, trimethylene and tetramethylene, in any of which one methylene may bear 1 or 2 methyl substituents.

A particular value for $B^1$ when it is a 5 or 6-membered saturated or unsaturated heterocyclic ring containing a single hetero atom selected from oxygen, sulphur or nitrogen includes, for example, a thienyl, furyl, pyrrolyl, pyrrolidinyl, pyridyl and piperidyl ring.

A particular value for $B^1$ when it is a 5 or 6-membered saturated or unsaturated heterocyclic ring containing two heteroatoms one of which is nitrogen and the other is oxygen, sulphur or nitrogen includes, for example, an imidazolyl, imidazolidinyl, pyrazolyl, pyrazolinyl, thiazolyl, thiazolinyl, oxazolyl, oxazolidinyl, pyrimidinyl, pyrazinyl, pyridazinyl, piperazinyl, morpholinyl and thiomorpholinyl ring.

A particular value for an optional alkyl substituent on $B^1$ is, for example, methyl or ethyl and for an optional alkoxy substituent is, for example, methoxy or ethoxy.

A particular value for $R^8$ when it is a non-toxic, biodegradable residue of a physiologically acceptable alcohol or phenol is, for example, a residue derived from a (1–6C)alkanol such as methanol or ethanol, or phenol, glycerol or the like.

A particular value for $R^9$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on a phenyl moiety of $R^1$, $R^2$, $R^3$ or $R^9$ include, by way of example, for halogeno: fluoro, chloro and bromo; for alkyl: methyl and ethyl; and for alkoxy: methoxy and ethoxy.

A specific value for X which is of particular interest is, for example, p-phenylene.

A preferred value for $R^1$ or $R^3$ is, for example, methyl or ethyl.

A preferred value for $R^2$ is, for example, hydrogen.

A preferred value for $R^4$ is, for example, benzoyl, substituted phenyl, or a group of the formula —$A^1.B^1$ wherein $A^1$ is a direct bond and $B^1$ is a pyridyl ring, particularly a 4-pyridyl ring, or $A^1$ is a methylene or carbonyl group and $B^1$ is piperidyl, morpholinyl or imidazolyl linked to $A^1$ by a ring nitrogen atom.

A preferred value for $A^1$ includes, for example, when it is a methylene group, a carbonyl group and a direct bond.

A preferred value for $R^6$, $R^7$ or $R^8$ is, for example, hydrogen.

A preferred value for Z is, for example, 1H-tetrazol-5-yl and which is especially preferred when attached ortho to the group X.

A particularly preferred combination of values is, for example, when $R^1$ and $R^3$ are both alkyl and $R^2$ is hydrogen.

A preferred group of compounds of the formula I comprises those compounds of the formula I wherein X is p-phenylene and Z is 1H-tetrazol-5-yl, and wherein $R^1$, $R^2$, $R^3$, $R^4$, $R^5$, $R^6$ and $R^7$ have any of the values defined above, and the non-toxic salts thereof. Especially preferred within this group are those compounds wherein Z is at the ortho position relative to X.

A particularly preferred group of compounds of the invention comprises compounds of the formula Ia wherein $R^1$, $R^2$, $R^3$, $R^7$ and Z have any of the values defined above; Ra is hydrogen, (1–4C)alkyl, (1–4C)alkoxy, halogeno, trifluoromethyl, cyano or nitro, and Het. is a 5 or 6-membered saturated or unsaturated heterocyclic ring containing a single heteroatom selected from oxygen, sulphur and nitrogen or containing two heteroatoms one of which is nitrogen and the other is oxygen, sulphur or nitrogen, and optionally bearing a (1–4C)alkyl substituent; and the non-toxic salts thereof.

A further particularly preferred group of compounds of the invention comprises compounds of the formula Ib wherein $R^1$, $R^2$, $R^3$, $R^7$ and Z have any of the meanings defined above; Ra is hydrogen, (1–4C)alkyl, (1–4C)alkoxy, halogeno, trifluoromethyl, cyano or nitro; and Rb and Rc are independently selected from hydrogen, (1–4C)alkyl, (1–4C)alkoxy, halogeno, cyano, trifluoromethyl, nitro, hydroxy, carboxy, (1–4C)alkanoylamino, (1–4C)alkanoyl, fluoro(1–4C)alkoxy, hydroxy(1–4C)alkyl, (1–4C)alkoxy(1–4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1–4C)alkoxycarbonyl, (1–4C)alkanesulphonamido, (1–4C)alkyl.S(O)$_n$-[in which n is zero, 1 or 2], 1H-tetrazol-5-yl, phenyl, phenoxy, benzyloxy, benzyloxycarbonyl, benzamido and benzenesulphonamido, the benzene moiety of the last six groups optionally bearing a halogeno, (1–4C)alkyl or (1–4C)alkoxy substituent; and the non-toxic salts thereof.

A yet further particularly preferred group of compounds of the invention comprises compounds of the formula Ic wherein $R^1$, $R^2$, $R^3$, $R^7$ and Z have any of the meanings defined above; Ra is hydrogen, (1–4C)alkyl, (1–4C)alkoxy, halogeno, trifluoromethyl, cyano or nitro; Rd is selected from nitro, hydroxy, carboxy, (1–4C)alkanoylamino, (1–4C)alkanoyl, fluoro(1–4C)alkoxy, hydroxy(1–4C)alkyl, (1–4C)alkoxy(1–4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1–4C)alkoxycarbonyl, (1–4C)alkanesulphonamido, (1–4C)alkyl.S(O)$_n$-[in which n is zero, 1 or 2], 1H-tetrazol-5yl, phenyl, phenoxy, benzyloxy, benzyloxycarbonyl, benzamido and benzenesulphonamido, the benzene moiety of the last six groups optionally bearing a halogeno, (1–4C)alkyl or (1–4C)alkoxy substituent; and Re is selected from hydrogen, (1–4C)alkyl, (1–4C)alkoxy, halogeno, cyano, trifluoromethyl and any of the values defined for Rd; and the non-toxic salts thereof.

A still further particularly preferred group of compounds of the invention comprises compounds of the formula Id wherein $R^1$, $R^2$, $R^3$, $R^7$ and Z have any of the meanings defined above; Ra is hydrogen, (1–4C)alkyl, (1–4C)alkoxy, halogeno, trifluoromethyl, cyano or nitro; $A^2$ is a methylene or carbonyl group and $B^2$ is a 5 or 6-membered saturated or unsaturated heterocyclic ring containing a single heteroatom selected from oxygen, sulphur and nitrogen or containing two heteroatoms one of which is nitrogen and the other is oxygen, sulphur or nitrogen, and wherein $B^2$ optionally bears a (1–4C)alkyl substituent; and the non-toxic salts thereof.

Preferably within the particularly preferred groups of compounds of the formula Ia, Ib, Ic and Id defined above, Z is 1H-tetrazol-5-yl, and especially when Z is at the ortho position relative to the adjacent phenyl ring.

Compounds of the invention which are of particular interest include, for example, the specific embodiments set out hereinafter in the accompanying Examples. Of these, the compounds of formula I described in Examples 3, 4, 8 and 9 are of special interest and these compounds, or a non-toxic salt thereof, are provided as a further feature of the invention.

Although all of the formula I compounds can form salts with suitable acids, it will be appreciated that those compounds of formula I wherein Z is other than an ester group or in which $R^2$ or $R^4$ bear a carboxy group can form salts with bases as well as with acids. Particularly suitable non-toxic salts for such compounds therefore also include, for example, salts with bases affording physiologically acceptable cations, for example, alkali metal (such as sodium and potassium), alkaline earth metal (such as magnesium and calcium), aluminum and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —CO.OR$^8$ in which R$^8$ is hydrogen), a carboxylic acid derivative of the formula II, in which Q is a protected carboxy group selected from (1–6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1–4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°–120° C., depending on the reactivity of the group Q. In general, when Q is carbamoyl, temperatures in the range, for example, 40°–120° C. are required to effect the hydrolysis.

Alternatively, when Q is benzyloxycarbonyl the conversion may also be performed by hydrogenolysis, for example using hydrogen at 1–3 bar in the presence of a suitable catalyst, such as palladium on charcoal or on calcium sulphate, in a suitable solvent or diluent such as a (1–4C)alkanol (typically ethanol or 2-propanol) and at a temperature in the range, for example, 0°–40° C.

Further, when Q is t-butoxycarbonyl, the conversion may also be carried out by hydrolysis at a temperature in the range, for example, 0°–100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of the formula IX with a trialkyltin azide, such as tributyltin azide, or triphenyltin azide respectively. The reaction is conveniently carried out in a suitable solvent or diluent, such as toluene or xylene, and at a temperature in the range, for example, 50°-150° C. The nitriles of the formula IX may be obtained, for example, by alkylation of a pyridone of the formula IV wherein $R^1$ and $R^3$ are other than hydrogen with a nitrile of the formula X wherein Hal. stands for a suitable leaving group such as chloro, bromo, iodo, methanesulphonyloxy or p-toluenesulphonyloxy, using similar conditions to those used in process (c) described hereinafter. The necessary compounds of formula X may be made by standard procedures such as that illustrated in Scheme 1 for compounds in which X is phenylene, or from a compound of the formula XI using methods of organic chemistry well known in the art. Alternatively, the nitriles of the formula IX may be obtained from stepwise conversion of a compound of formula I wherein Z is a group of the formula —$CO.OR^8$ under standard conditions.

The nitriles of the formula IX may also be obtained, for example, by reaction of a pyridine of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) with an alcohol of the formula XI, using similar conditions to those used in process (d) described hereinafter. The alcohol of the formula XI may be obtained, for example, by standard procedures such as that illustrated in Scheme 1 for compounds in which X is phenylene, or by analogy with Scheme 2.

Alternatively, compounds of the formula III may be obtained, for example, by reaction of a pyridine of the formula VII wherein $Y^1$ is as defined above with an alcohol of the formula XII under similar conditions to those described in process (d) hereinafter. The alcohols of formula XII may be obtained, for example, from the appropriate bromomethyl compound by standard procedures such as those shown in Scheme 2.

As a further alternative, the compounds of formula III may be obtained, for example, as shown in Scheme 6 for compounds in which X is phenylene and $R^4$ is a group of the formula -$A^1.B^1$ wherein $A^1$ is a methylene group and $B^1$ is a heterocyclic ring linked to $A^1$ by a nitrogen atom (or by analogy therewith), the pyridone starting materials for which may be obtained using (or by analogy with) the procedure described in *Monatshefte fur Chemie*, 1969, 100, 132 for the preparation of ethyl 1,4-dihydro-2,6-dimethyl-4-oxopyridine-3-carboxylate, or by analogy with Scheme 3.

c) A pyridone of the formula IV wherein $R^1$ and $R^3$ are other than hydrogen is alkylated with a compound of the formula V wherein Hal. stands for a suitable leaving group such as chloro, bromo, iodo, methanesulphonyloxy or p-toluenesulphonyloxy.

The reaction is generally carried out in the presence of a suitable base, for example, an alkali metal alkoxide such as sodium methoxide or sodium ethoxide or an alkali metal hydride such as sodium hydride or an alkali metal carbonate such as sodium or potassium carbonate, or an organic base such as diisopropylethylamine and in a suitable solvent or diluent, for example, a (1–4C)alkanol such as methanol or ethanol when an alkali metal alkoxide is used, or in a polar solvent such as N,N-dimethylformamide or N-methylpyrrolidone and at a temperature in the range, for example, 10°-100° C. Alternatively, a quaternary ammonium hydroxide may be used in a mixture of an aqueous and non-aqueous solvent such as water and dichloromethane. In carrying out process (c), when $R^8$ is hydrogen in the starting material of formula V, about two molecular equivalents of a suitable base is generally required, whereas when $R^8$ is other than hydrogen the presence of one molecular equivalent of a suitable base is generally sufficient.

Procedure (c) is particularly suitable for the production of those compounds of the formula I in which Z is a group of the formula —$CO.OR^8$ in which $R^8$ is other than hydrogen, for example wherein $R^8$ is (1–6C)alkyl, benzyl or phenyl, which compounds are also starting materials of formula II for the reaction described in (a) above. Similarly, using an analogous procedure, but starting with the appropriate halomethyl tetrazolyl derivative of the formula VI, the starting materials of the formula III may be obtained for procedure (b).

Many of the pyridones of formula IV are already known and the remainder can be made by analogy therewith using standard procedures of organic chemistry well known in the art, for example as described in standard works of heterocyclic chemistry such as that edited by Elderfield, or as illustrated in Scheme 3, 4 or 5. The necessary compounds of the formula V (and also of formula VI) may be made by standard procedures such as those which are illustrated in Scheme 1 for compounds in which X is phenylene. Alternatively, a compound of the formula V or formula VI may be obtained from a formula VIII compound (in which Z is the group $CO.OR^8$) or formula XII compound respectively, using procedures of organic chemistry well known in the art.

Compounds of the formula VI wherein X is phenylene and $R^5$ and $R^6$ are both hydrogen may also be conveniently obtained by reaction of a Grignard reagent, formed from a suitably substituted 4-bromotoluene, with a trialkyltin halide, such as tributyltin chloride, followed by reaction of the resulting (substituted)-phenyltrialkyltin compound with a bromobenzonitrile in the presence of a palladium(O) catalyst, such as tetrakis(triphenylphosphine)palladium, and azo(-bisisobutyronitrile). The resultant substituted 4'-methylbiphenylcarbonitrile may then be converted to a compound of the formula VI by carrying out steps (b), (c)

and (d) in a similar manner to that shown in Scheme 1. Alternatively, suitably substituted 4'-methylbiphenylcarbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(-bisisobutyronitrile).

(d) A pyridine derivative of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) is reacted with an alcohol of the formula VIII.

The reaction is generally carried out in the presence of a suitable base, for example an alkali metal alkoxide such as sodium methoxide or ethoxide or an alkali metal hydride such as sodium hydride and in a suitable solvent or diluent, for example a (1–4C)alkanol such as methanol or ethanol when an alkali metal alkoxide is used, or a polar solvent such as N,N-dimethylformamide. Alternatively, an alcohol of the formula VIII may be used in the form of its preformed alkali metal salt (when Z is a non-acidic group) or di-alkali metal salt (when Z is an acidic group). The reaction is usually performed at a temperature in the range of 40° to 120° C. The reaction may in preference be carried out with a formula VIII compound in the presence of an acid catalyst such as p-toluenesulphonic acid, instead of under basic conditions, and in the presence of an inert solvent or diluent such as toluene. Yet a further alternative is to heat together a compound of the formula VII with a formula VIII compound at an elevated temperature, for example, at a temperature in the range 120°–180° C. and in the absence of solvent or in the presence of a high boiling solvent or diluent such as diphenyl ether.

Pyridine derivatives of the formula VII wherein $Y^1$ is halogeno may be obtained, for example, by halogenation of the corresponding pyridones of formula IV, for example, by reaction with phosphorous oxychloride in the absence of a solvent, or in the presence of an inert solvent or diluent such as toluene or dioxane, and at a temperature in the range 60°–110° C. Compounds of the formula VII wherein $Y^1$ is methanesulphonyloxy, p-toluenesulphonyloxy or trifluoromethanesulphonyloxy and $R^1$ and $R^3$ are other than hydrogen may be obtained, for example, by acylation of the corresponding pyridones of formula IV with the corresponding sulphonyl chloride under standard conditions. Compounds of the formula VII wherein $Y^1$ is methanesulphonyl may be obtained from alkylation of the corresponding mercaptopyridines followed by oxidation under standard conditions. The alcohols of the formula VIII are known or can be prepared by standard procedures well known in the art, for example, by analogy with Scheme 2 or deprotection of a compound obtained thereby.

Whereafter, those compounds of formula I wherein Z is 1H-tetrazol-5-yl may be obtained by stepwise conversion of a compound of the formula I wherein Z is a group of the formula —$CO.OR^8$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is —CO.NH.(1H-tetrazol-5-yl), a group of the formula —$CO.NH.SO_2R^9$ or a group of the formula —$CO.OR^8$ in which $R^8$ is other than hydrogen, may be obtained, for example, by reacting a carboxylic acid of the formula I in which Z is carboxy (or a reactive derivative of said acid) with 5-aminotetrazole, a sulphonamide of the formula $NH_2.SO_2R^9$ or a salt thereof (for example, an alkali metal salt), or a hydroxy compound of the formula $HO.R^8$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or, for the preparation of a compound of the formula I wherein Z is a group of the formula —$CO.NH.SO_2R^9$ or a group of the formula —$CO.OR^8$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°–60° C.

Whereafter, when an N-oxide derivative of a compound of the formula I is required, a compound of the formula I is oxidised. Suitable oxidising agents include those well known in the art for the conversion of nitrogen heterocycles to their corresponding N-oxide derivatives, for example, hydrogen peroxide or an organic peracid such as m-chloroperbenzoic acid or peracetic acid. The oxidation is preferably carried out in a suitable conventional solvent or diluent for such oxidations, for example dichloromethane, chloroform or acetic acid, and at a temperature in the general range, for example 0° to 80° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

According to a further aspect of the invention, there is provided a process for the manufacture of a compound of the formula I wherein Z is tetrazolyl, X is p-phenylene optionally bearing a substituent selected from (1–4C)alkyl, (1–4C)alkoxy, halogeno, trifluoromethyl, cyano and nitro, $R^5$ and $R^6$ are both hydrogen, and $R^1$, $R^2$, $R^3$, $R^4$, $R^7$, have any of the meanings defined hereinbefore; which comprises reaction of a compound of the formula XIII wherein $P^1$ is an electron-deficient phenyl group, or is a pyridyl or pyrimidyl group; $R^{10}$ is hydrogen, (1–4C)alkyl, (1–4C)alkoxy, halogeno, trifluoromethyl, cyano or nitro; and $R^1$, $R^2$, $R^3$, $R^4$ and $R^7$ have any of the values defined above with a base selected from an alkali metal hydroxide, (1-12C)alkanolate, (1-12C)alkanethiolate, phenolate, thiophenolate or diphenylphosphide, wherein any phenyl ring of the latter three groups may optionally bear a (1–4C)alkyl, (1–4C)alkoxy or halogeno group.

A particular value for $P^1$ when it is an electron-deficient phenyl group includes, for example, a phenyl group bearing 1, 2 or 3 electron-withdrawing groups independently selected from halogeno (typically chloro or bromo), nitro, cyano and trifluoromethyl.

A particular value for $R^{10}$ when it is alkyl is, for example, methyl or ethyl; when it is alkoxy is, for example, methoxy or ethoxy; and when it is halogeno is, for example, fluoro, chloro, bromo or iodo.

A suitable base includes, for example: for an alkali metal hydroxide: sodium or potassium hydroxide; for an alkali metal alkanolate: an alkali metal (1-8C)alkanolate, for example an alkali metal (1–4C)alkoxide, such as sodium or potassium methoxide, ethoxide, propoxide or butoxide; for an alkali metal alkanethiolate: an alkali metal (1-8C)alkanethiolate, for example an alkali metal (1–4C)alkanethiolate such as sodium or potassium methanethiolate, ethanethiolate, propanethiolate or butanethiolate.

A particular value for an optional substituent on a phenyl group of an alkali metal phenolate, thiophenolate or diphenylphosphide, when it is alkyl is, for example, methyl or ethyl; when it is alkoxy is, for example, methoxy or ethoxy; and when it is halogeno is, for example, fluoro, chloro or bromo.

A preferred value for $P^1$ is, for example, an electron-deficient phenyl group, particularly a nitrophenyl group, especially 4-nitrophenyl.

A preferred value for X is, for example, when it is unsubstituted p-phenylene.

A particularly preferred base is an alkali metal alkanethiolate such as sodium or potassium propanethiolate, an alkali metal alkanolate such as sodium or potassium ethoxide, or an alkali metal thiophenolate such as sodium or potassium 4-fluorothiophenolate.

It will be appreciated that when the base is an alkali metal alkanolate, alkanethiolate, phenolate, thiophenolate or diphenylphosphide, it may be generated in situ from the corresponding alkanol, alkanethiol, phenol, thiophenol or diphenylphosphine with a suitable alkali metal base such as an alkali metal hydride, for example, lithium, potassium or sodium hydride.

The process of the invention is particularly useful for the preparation of compounds of the formula I wherein the tetrazolyl group is at the ortho position relative to the adjacent phenyl group.

The reaction is conveniently carried out in a suitable inert organic solvent or diluent, for example, a polar solvent such as N,N-dimethylformamide or N-methylpyrrolidone. Alternatively, an alkanol such as methanol or ethanol may be used, for example, when an alkali metal hydroxide or alkoxide such as sodium or potassium hydroxide, methoxide or ethoxide is employed. The reaction is generally carried out at a temperature in the range, for example, −30° C. to 50° C. It will be appreciated that the choice of temperature will depend on the nature of the base employed. For example, when an alkali metal alkanethiolate or alkanolate is used, a temperature in the range of 0° C. to ambient temperature is preferred.

Compounds of the formula XIII may be obtained by reaction of a boronic acid of the formula XIV with a compound of the formula XV wherein $P^1$ is an electron-deficient phenyl group having any of the meanings defined above and W is a bromo, iodo or trifluoromethanesulphonyloxy group, in the presence of a palladium(O) catalyst, such as tetrakis(triphenylphosphine)palladium, and azo(bisisobutyronitrile). The reaction is preferably carried out in the presence of a base, such as sodium or potassium carbonate, in an inert solvent or diluent, for example, a hydrocarbon such as toluene or xylene, an ether, such as dioxan or tetrahydrofuran, an (1–4C)alkanol such as methanol or ethanol, water, or mixture thereof, for example a mixture of water, methanol and toluene, and at a temperature in the range of, for example, 50° C. to 150° C., and conveniently at or about the reflux temperature of the solvent or mixture of solvents used.

Compounds of the formula XIV may be obtained, for example, by heating at reflux a 4-methylphenylboronic acid in a solvent such as methyl chloroform with azeotropic removal of water, followed by radical bromination of the product which may be carried out in situ, for example with bromine and azo(bisisobutyronitrile). The resultant 4-bromomethylphenylboronic acid anhydride may then be used to alkylate a compound of the formula IV (using similar alkylation conditions to those used in process (c) described above), followed by subsequent acidic hydrolysis, to give a formula XIV compound. Alternatively the product from the alkylation step prior to hydrolysis may be isolated and reacted directly with a compound of the formula XV under similar conditions to those described above to obtain a formula XIII compound directly. In a yet further alternative procedure, a 4-methylphenylboronic acid and an appropriate alkanediol, for example 2,2-dimethylpropan-1,3-diol, may be heated at reflux in a solvent (such as cyclohexane) with azeotropic removal of water followed by free radical bromination of the product, which may be carried out in situ. The resultant bromomethyl compound may then be reacted using analogous procedures to those described above for the 4-bromomethylphenylboronic acid anhydride to obtain a formula XIV compound or a compound of the formula XIII directly.

Compounds of the formula XV may be obtained, for example, as shown in Scheme 7.

Whereafter, an N-oxide or a non-toxic salt or an optically active form of a compound of the formula I may be obtained as described above if desired.

Certain of the intermediates defined herein are novel, for example the compounds of the formula II, III and IX, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The compounds of the invention may also be useful for the treatment of ocular hypertension, glaucoma, cognitive disorders (such as Alzheimer's disease, amnesia, senile dementia and learning disorders), as well as other diseases such as renal failure, cardiac insufficiency, post-myocardial infarction, cerebrovascular disorders, anxiety, depression and certain mental illnesses such as schizophrenia.

The antagonism of one or more of the physiological actions of AII and, in particular, the antagonism of the interaction of AII with the receptors which mediate its effects on a target tissue, may be assessed using one or more of the following, routine laboratory procedures:

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}M$ are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, acidic compounds of formula I as defined above show significant inhibition in Test B at a final concentration of 50 micromolar or much less. [Note: Compounds of formula I wherein Z is a group of the formula —CO.OR$^8$ in which R$^8$ is other than hydrogen in general show only weak activity in the in vitro Tests A or B.]

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect. Test D: This in vivo involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of formula I, the compound of Example 3 gave the following results in tests A and C described above:

In test A: an $IC_{50}$ of $0.55 \times 10^{-8}M$;

In test C: $ED_{50}$ of 0.18 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt or N-oxide thereof as defined above, together with a pharmaceutically acceptable diluent or carrier. Such compositions will conveniently be in a form suitable for oral adminstration (e.g. as a tablet, capsule, solution, suspension or emulsion) or parenteral administration (e.g. as an injectable aqueous or oily solution, or injectable emulsion).

The compounds of formula I, or a non-toxic salt thereof, may also be advantageously administered for therapeutic or prophylactic purposes together with another pharmacological agent known in the general art to be of value in treating one or more of the diseases or medical conditions referred to hereinabove, such as a beta-adrenergic blocker (for example atenolol), a calcium channel blocker (for example nifedipine), an angiotensin converting enzyme (ACE) inhibitor (for example lisinopril) or a diuretic (for example furosemide or hydrochlorothiazide). It is to be understood that such combination therapy constitutes a further aspect of the present invention.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°–26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1$H NMR spectra were normally determined at 200 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(vi) $^{13}$C NMR spectra were normally determined at 100 MHz ,in CDCl$_3$ or d$_6$-dimethylsulphoxide (d$_6$-DMSO) using the solvent signal as internal standard, and are expressed as chemical shifts (delta values) in parts per million relative to TMS; and (vii) all end-products had satisfactory microanalyses.

EXAMPLE 1

6M Hydrochloric acid (1 ml) was added to a solution of 2,6-dimethyl-3-(4-pyridyl)-4-[(2'-(2-triphenylmethyl-2H-tetrazol-5-yl)biphenyl-4-yl)methoxy]pyridine (A) (800 mg) in dioxan (20 ml) and the mixture was stirred for 3 hours. Volatile material was removed by evaporation and the residue triturated with ether. The ether was separated and the residue was dissolved in methanol. Ether was added to precipitate the product and the solvent was again separated. The residue was then triturated with ether to give 2,6-dimethyl-3-(4-pyridyl)-4-[(2'(1H-tetrazol-5-yl)biphenyl-4-yl)methoxy]pyridine dihydochloride (0.51 g), as a solid, m.p. 180° C. (decomposition); NMR (d$_6$-DMSO, d$_4$-acetic acid): 2.4(s,3H), 2.75(s,3H), 5.45(s,2H), 7.1(d,2H), 7.25(d,2H), 7.5–7.8 (complex m,5H), 8.0(d,2H), 9.0(d,2H); mass spectrum (positive fast atom bombardment (+ve FAB) DMSO/nitrobenzyl alcohol): 869.4 (2M+H)+; microanalysis, found: C,56.7; H,5.3; N,14.9; H$_2$O,8%; C$_{26}$H$_{22}$N$_6$O.2HCl.2.5H$_2$O.0.2(C$_2$H$_5$)$_2$O requires C,56.7; H,5.5; N,14.8%.

The starting material (A) was obtained as follows:

(i) Diketene (30 g) was added dropwise to a stirred solution of 1-(4-pyridyl)-2-propanone (20.25 g) in acetic acid (100 ml) at 0° C. The mixture was allowed to warm to ambient temperature and stirred for 90 minutes. The mixture was heated to 50° and stirred for a further 90 minutes. The solvent was removed by evaporation and the residue purified by flash chromatography, eluting with dichloromethane/methanol (19:1 v/v) to give 2,6-dimethyl-3-(4-pyridyl)-4H-pyran-4-one (C) (21.6 g), as a yellow solid; NMR (CDCl$_3$): 2.28(s,3H), 2.35(s,3H), 6.2(s,1H), 7.2(dd,2H), 8.65(dd,2H); mass spectrum (chemical ionisation, ammonia): 202 (M+H)+.

(ii) A solution of compound C (8.4 g) in saturated ethanolic ammonia (700 ml) was heated at 120° C. in an autoclave for 67 hours. The solvent was removed by evaporation and the residue recrystallised from ethyl acetate/methanol to give 1,4-dihydro-2,6-dimethyl-4-oxo-3-(4-pyridyl)pyridine (B) (5.1 g) as a brown solid; NMR (d$_6$-DMSO): 2.1(s,3H), 2.2(s,3H), 6.0(s,1H), 7.2(d,2H), 8.5(broad s,2H), 11.2(broad s,1H); mass spectrum (chemical ionisation, ammonia): 201 (M+H)+.

(iii) Sodium hydride (60% dispersion in mineral oil; 130 mg) was added to a stirred solution of compound B (0.6 g) in N,N-dimethylformamide (DMF) (10 ml). The mixture was stirred at 50° C. for 1 hour and then a solution of 5-[2-(4'-bromomethylbiphenylyl)]-2-triphenylmethyl-2H-tetrazole (1.9 g) (obtained as described in European patent application, publication no. 0291969) in DMF (20 ml) was added. The solution was stirred at 50° C. for 1 hour and then at ambient temperature for 16 hours. The solvent was removed by evaporation and the residue purified by flash chromatography, eluting with dichloromethane/methanol (9:1 v/v) to give 2,6-dimethyl-3-(4-pyridyl)-4-[(2'-(2-triphenylmethyl-2H-tetrazol-5-yl)biphenyl-4-yl)methoxy]pyridine (A) (0.97 g) as a solid, m.p. 178° C. (decomposition); NMR (CDCl$_3$): 2.3(s,3H), 2.5(s,3H), 5.0(s,2H), 6.65(s,1H), 6.85–7.0 (complex m,8H), 7.0–7.5 (complex m,16H), 7.9–8.0(m,1H), 8.6–8.7(d,2H); mass spectrum (+ve FAB, DMSO/nitrobenzyl alcohol): 677 (M+H)+.

EXAMPLES 2-5

Using an analogous procedure to that described in Example 1, but starting from the appropriate compound of formula III wherein L is triphenylmethyl, the following compounds of formula I were obtained in yields of 40-97%.

EXAMPLE 2

2,6-dimethyl-3-(2-pyridyl)-4-[(2'-(1H-tetrazol-5-yl)biphenyl-4-yl)methoxy]pyridine dihydrochloride, as a solid m.p. 64°–74° C. (decomposition); NMR (d$_6$-DMSO/d$_4$-acetic acid): 2.5(s,3H), 2.8(s,3H), 5.4(s,2H), 7.1(d,2H), 7.3(d,2H), 7.5–7.9 (complex m,7H), 8.2–8.3(m,1H), 8.9(d,1H); mass spectrum (+ve FAB, DMSO/nitrobenzyl alcohol): 435 (M+H)+; microanalysis, found: C,59.1; H,5.2; N,15.2; H$_2$O,3.2%; C$_{26}$H$_{22}$N$_6$O.2HCl.1H$_2$O.0.2(C$_2$H$_5$)$_2$O requires C,59.5; H,5.2; N,15.5%.

EXAMPLE 3

6-ethyl-2-methyl-3-(4-pyridyl)-4-[(2'-(1H-tetrazol-5-yl)biphenyl-4-yl)methoxy]pyridine dihydrochloride as a solid, m.p. 194°–198° C. (decomposition); NMR (d$_6$-DMSO/d$_4$-acetic acid): 1.4(t,3H), 2.55(s,3H), 3.1(q,2H), 5.5(s,2H), 7.1(d,2H), 7.3(d,2H), 7.5–7.8(m,5H), 8.1(d,2H), 9.0(d,2H); mass spectrum (+ve FAB, DMSO/nitrobenzyl alcohol): 449 (M+H)+.

EXAMPLE 4

3-benzoyl-2,6-dimethyl-4-[(2'-(1H -tetrazol-5-yl)-biphenyl-4-yl)methoxy]pyridine hydrochloride as a solid, m.p. 198°–200° C. (decomposition); NMR ($d_6$-DMSO/$d_4$-acetic acid): 2.5(s,3H), 2.8(s,3H), 5.4(s,2H), 7.05(dd,4H), 7.5–7.9 (complex m,10H); mass spectrum (+ve FAB, DMSO/nitrobenzyl alcohol): 462 $(M+H)^+$; microanalysis, found: C,66.9; H,5.3; N,13.9%; $C_{28}H_{43}N_5O_2.HCl.0.04(C_2H_5)_2O.0.08CH_3OH$ requires: C,67.0; H,5.0; N,13.9%.

EXAMPLE 5

1-[3-(2,6-diethyl-4-(2'-(1H -tetrazol-5-yl)biphenyl-4-yl)methoxy)pyridylcarbonyl]piperidine hydrochloride as a solid, m.p. 130°–133° C. (decomposition); NMR ($d_6$-DMSO/$d_4$-acetic acid): 1.3–1.8(complex m,14H), 2.7–3.2(m,6H), 3.5–3.8(m,2H), 5.45(s,2H), 7.2(d,2H), 7.4(d,2H), 7.5–7.8(m,5H); mass spectrum (+ve FAB, DMSO/nitrobenzyl alcohol): 462$(M+H)^+$; microanalysis, found: C,64.7; H,6.8; N,14.7; $H_2O$,1.5%; $C_{29}H_{32}N_6O_2.HCl.0.32(C_2H_5)_2O.0.5H_2O$ requires: C,64.3; H,6.6; N,14.8%.

The necessary starting materials of formula III used in Examples 2–5, corresponding to starting material A in Example 1, were obtained in yields of 54–86% using an analogous procedure to that described in Example 1 as follows:

EXAMPLE 2A 2,6-dimethyl-3-(2-pyridyl)-4-[(2'-(2-triphenylmethyl-2H-tetrazol-5-yl)biphenyl-4-yl)methoxy]pyridine as a foam; NMR: (CDCl$_3$): 2.3(s,3H), 2.5(s,3H), 5.2(s,2H), 6.6(s,1H), 6.85–7.0 (complex m,8H), 7.05(d,2H), 7.1–7.4 (complex m,13H), 7.4–7.5(m,2H), 7.6–7.75(m,1H), 7.9–8.0(m,1H), 8.7–8.8(m,1H); mass spectrum (+ve FAB, methanol/nitrobenzyl alcohol): 677 $(M+H)^+$.

EXAMPLE 3A 6-ethyl-2-methyl-3-(4-pyridyl)-4-[(2'-(2-triphenyl-methyl-2H-tetrazol-5-yl)biphenyl-4-yl)methoxy]pyridine as a solid, m.p. 127°–132° C. (decomposition); NMR (CDCl$_3$): 1.3(t,3H), 2.35(s,3H), 5.0(s,2H), 6.7(s,1H), 6.85–7.0 (complex m,8H), 7.05–7.15(m,2H), 7.2–7.5 (complex m,14H), 7.85–7.95(m,1H), 8.6–8.7(broad s,2H); mass spectrum (+ve FAB, DMSO/nitrobenzyl alcohol): 691 $(M+H)^+$.

EXAMPLE 4A 3-benzoyl-2,6-dimethyl-4-[(2'-(2-triphenylmethyl-2H-tetrazol-5-yl)biphenyl-4-yl)methoxy]pyridine isolated as a solid, m.p. 84°–91° C.; NMR (CDCl$_3$): 2.4(s,3H), 2.7(s,3H), 4.9(s,2H), 6.65(s,1H), 8.7(s,2H), 6.8–7.0 (complex m,8H), 7.1–7.6 (complex m,15H), 7.8–8.0(m,3H); mass spectrum (+ve FAB, DMSO/nitrobenzyl alcohol/methanol): 704 $(M+H)^+$.

EXAMPLE 5A

1-[3-(2,6-diethyl-4-(2'-(2-triphenylmethyl-2H-tetrazol-5-yl)biphenyl-4-yl)methoxy)pyridylcarbonyl]-piperidine isolated as a solid, m.p. 73°–77° C.; NMR (CDCl$_3$): 1.2–1.3(m,6H), 1.4(m,2H), 1.6(m,4H), 2.7–2.85(m,4H), 3.2(t,2H), 3.7(m,2H), 5.0(s,2H), 6.6(s,1H), 6.85–7.0(m,6H), 7.1–7.6 (complex m,16H), 7.9(m,1H); mass spectrum (+ve FAB; DMSO/methanol/nitrobenzyl alcohol): 739 $(M+H)^+$.

The necessary starting materials of formula IV used in Examples 2–5, corresponding to compound B in Example 1, were obtained as follows:

EXAMPLE 2B 1,4-dihydro-2,6-dimethyl-4-oxo-3-(2-pyridyl)pyridine as a solid, m.p. 213°–218° C. (decomposition); NMR ($d_6$-DMSO): 2.1(s,3H), 2.2(s,3H), 6.0(s,1H), 7.2–7.3(m,1H), 7.4(d,1H), 7.7–7.8(m,1H), 8.6(d,1H), 11.2(broad s,1H); mass spectrum (chemical ionisation, ammonia): 201 $(M+H)^+$, using an analogous procedure to that described in Example 1, part (ii), starting from 2,6-dimethyl-3-(2-pyridyl)-4H-pyran-4-one, itself obtained as a solid, m.p. 70°–73° C.; NMR (CDCl$_3$): 2.3(2s,6H), 6.2(s,1H), 7.2–7.3(m,1H), 7.4–7.5(m,1H), 7.7–7.8(m,1H), 8.6–8.7(m,1H); mass spectrum (chemical ionisation, ammonia): 202 $(M+H)^+$; microanalysis, found: C,71.5; H,5.7; N,7.0%; $C_{12}H_{11}NO_3$ requires: C,71.6; H,5.5; N,7.0%, using an analogous procedure to that described in Example 1, part (i), but starting from 1-(2-pyridyl)-2-propanone (obtained as described in *J. Org. Chem.*, 1978, 43, 2286).

EXAMPLE 3B 1,4-dihydro-6-ethyl-2-methyl-4-oxo-3-(4-pyridyl)-pyridine as a solid; NMR ($d_6$-DMSO): 1.2(t,3H), 2.1(s,3H), 2.5(q,2H), 6.0(s,1H), 7.2(dd,2H), 8.55(dd,2H); mass spectrum (chemical ionisation, ammonia): 215 $(M+H)^+$, using an analogous procedure to that described in Example 1, part (ii), starting from 6-ethyl-2-methyl-3-(4-pyridyl)-4H-pyran-4-one itself obtained as follows:

A mixture of 1-(4-pyridyl)-2-propanone (1.35 g) and 5-(1-hydroxypropylidine)-2,2-dimethyl-1,3-dioxane-4,6-dione (4.0 g) [obtained as described in J. Org. Chem., 1978, 43, 2087] was heated at 120° C. for 2 hours. The residue was cooled to ambient temperature and purified by flash chromatography, eluting with dichloromethane/methanol (19:1 v/v) to give 6-ethyl-2-methyl-3-(4-pyridyl)-4H-pyran-4-one (0.87 g), as a solid m.p. 122°–123° C.; NMR (CDCl$_3$): 1.3(t,3H), 2.2(s,3H), 2.6(q,2H), 6.2(s,1H), 7.2(dd,2H), 8.65(dd,2H); mass spectrum (chemical ionisation, ammonia): 216 $(M+H)^+$; microanalysis, found: C,72.4; H,6.3; N,6.5%; $C_{13}H_{13}NO_2$ requires: C,72.6; H,6.0; N,6.5%.

EXAMPLE 4B 3-benzoyl-1,4-dihydro-2,6-dimethyl-4-oxopyridine was obtained as described in *Monatshefte Fur Chemie*, 1969, 100, 132.

EXAMPLE 5B

1-[3-(2,6-diethyl-1,4-dihydro-4-oxo)pyridylcarbonyl]piperidine as a solid, m.p. 49°–54° C.; NMR ($d_6$-DMSO): 1.2(m,6H), 1.3–1.7(m,6H), 2.3–2.5(m,4H), 3.1–3.7(m,4H), 5.9(s,1H), 11.0(broad s,1H); mass spectrum (chemical ionisation, ammonia): 263$(M+H)^+$, using an analogous procedure to that described in *Tet. Lett.*, 1977, 4171 by refluxing a toluene solution of dimethylaluminium piperidide and methyl 2,6-diethyl-1,4-dihydro-4-oxopyridine-3-carboxylate itself obtained as follows:

A mixture of methyl 3-amino-2-pentenoate (7.3 g) and 5-(1-hydroxypropylidene)-2,2-dimethyl-1,3-dioxane-4,6-dione (23.0 g) was heated at 120° C. for 2 hours. The residue was cooled to ambient temperature, triturated with ether and the solid collected by filtration to give methyl 2,6-diethyl-1,4-dihydro-4-oxopyridine-3-carboxylate (5.2 g) as a pale yellow solid, m.p. 124°–127° C.; NMR (d$_6$-DMSO): 1.2(t,6H), 2.3–2.6(m,4H), 3.7(s,3H), 6.3(s,1H); mass spectrum (chemical ionisation, ammonia): 210 (M+H)$^+$.

EXAMPLE 6

6M Hydrochloric acid (2 ml) was added to a solution of 2,6-dimethyl-3-(4-morpholinomethyl)-4-[(2'-(2-triphenylmethyl-2H-tetrazol-5-yl)biphenyl-4-yl)methoxy]pyridine (D) (470 mg) in dioxan (10 ml) and the mixture was stirred for 3.5 hours. Volatile material was removed by evaporation and the residue was triturated with ether. The product was collected by filtration to give 2,6-dimethyl-3-(4-morpholinomethyl)-4-[(2'-(1H-tetrazol-5-yl)biphenyl-4-yl)methoxy]pyridine dihydrochloride (297 mg) as a solid, m.p. 177°–181° C., NMR (d$_6$-DMSO/d$_4$-acetic acid): 2.65(s,3H), 2.8(s,3H), 3.2(broad s,4H), 3.8(broad s,4H), 4.3(s,2H), 5.4(s,2H), 7.15–7.7 (complex m,9H); mass spectrum (+ve FAB, DMSO): 457(M+H)$^+$; microanalaysis, found: C,55.9; H,5.8; N,14.7; H$_2$O,3.1%; C$_{26}$H$_{28}$N$_6$O$_2$.2HCl.1-H$_2$O.0.1(C$_2$H$_5$)$_2$O requires: C,56.3; H,5.8; N,15.1%.

The starting material (D) was obtained as follows:

(i) Sodium hydride (60% dispersion in mineral oil; 206 mg) was added to a stirred solution of ethyl 1,4-dihydro-2,6-dimethyl-4-oxopyridine-3-carboxylate (1.0 g) (obtained as described in *Monatshefte fur Chemie.,* 1969, 100, 132) in DMF (25 ml). The mixture was stirred at 50° C. until evolution of hydrogen ceased and then 5-[2-(4'-bromomethylbiphenylyl)]-2-triphenylmethyl-2H-tetrazole (2.86 g) was added. The solution was stirred at 50° C. for 30 minutes and then at ambient temperature for 72 hours. The solvent was removed by evaporation and the residue partitioned between ethyl acetate (30 ml) and water (30 ml). The organic layer was separated, washed with saturated sodium chloride solution (30 ml) and dried (MgSO$_4$). The solvent was removed by evaporation and the residue purified by flash chromatography, eluting with ethyl acetate/hexane (1:1 v/v gradually changing to 9:1 v/v) to give ethyl 2,6-dimethyl-4-[(2'-(2-triphenylmethyl-2H-tetrazol-5-yl)biphenyl-4-yl)methoxy]pyridine-3-carboxylate (A) (2.38 g), as a foam; NMR (d$_6$-DMSO/d$_4$-acetic acid); 1.2(t,3H), 2.4(s,3H), 2.45(s,3H), 4.3(q,2H), 5.2(s,2H), 6.85–6.95(m,6H), 7.0(s,1H), 7.15(d,2H), 7.25–7.4 (complex m,11H), 7.45–7.75 (complex m,3H), 7.85(dd,1H); $^{13}$C NMR (d$_6$-DMSO): 69.0 (benzylic CH$_2$).

(ii) Lithium borohydride (66 mg) was added over a period of 10 minutes to a solution of compound A (800 mg) in tetrahydrofuran (THF) (25 ml) stirred at 0° C. under an atmosphere of argon. The solution was then stirred at ambient temperature for 16 hours, cooled to 0° C. and water (100 ml) was added. The mixture was extracted with dichloromethane (2×50 ml) and the extracts were washed with saturated sodium chloride solution (50 ml) and dried (MgSO$_4$). The solvent was removed by evaporation and the residue purified by flash chromatography, eluting with methanol/dichloromethane (1:19 v/v, to give 3-hydroxymethyl-2,6-dimethyl-4-[(2'-(2-triphenylmethyl-2H-tetrazol-5-yl)biphenyl-4-yl)methoxy]pyridine (B) (246 mg), as a foam; NMR (d$_6$-DMSO/d$_4$-acetic acid): 2.55(s,3H), 2.65(s,3H), 4.7(s,2H), 5.4(s,2H), 6.9–7.0(m,6H), 7.2(d,2H), 7.25–7.45(complex m,12H), 7.45–7.8(complex m,3H), 7.9(dd,1H).

(iii) Triethylamine (2.2 ml) and methanesulphonyl chloride (1.24 ml) were added to a solution of compound B (10.0 g) in dichloromethane (150 ml). The solution was left to stand for 20 hours and then diluted with water (150 ml). The organic phase was separated, washed with saturated sodium chloride solution (150 ml), and dried (MgSO$_4$). Volatile material was removed by evaporation and the residue was purified by flash chromatography, eluting with a mixture of methanol and dichlormethane (1:19 v/v) to give 3-chloromethyl-2,6-dimethyl-4-[(2'-(2-triphenylmethyl-2H-tetrazol-5-yl)biphenyl-4-yl)methoxy]pyridine (C) (8.5 g), as a white solid, m.p. 110°–112° C.; NMR (d$_6$-DMSO/d$_4$-acetic acid): 2.5(s,3H), 2.65(s,3H), 4.75(s,2H), 5.45(s,2H), 6.9–7.9 (complex m,24H).

(iv) Morpholine (0.07 ml) was added to a solution of triethylamine (0.11 ml) and compound C (0.5 gm) in dichloromethane (10 ml) and the mixture was stirred at ambient temperature for 16 hours. The mixture was washed with water, saturate sodium chloride solution and dried (MgSO$_4$). Solvent was removed by evaporation and the residue purified by flash chromatography, eluting with dichloromethane/methanol (3:97 v/v) increasing to (7:93 v/v) to give 2,6-dimethyl-3-(4-morpholinomethyl)-4-[(2'-(2-triphenylmethyl-2H-tetrazol-5-yl)biphenyl-4-yl)methoxy]pyridine (D) (0.48 g) as a solid, m.p. 84°–87° C.; NMR (CDCl$_3$): 2.45(s,3H), 2.45(m,4H), 2.65(s,3H), 3.55(s,2H), 3.65(t,4H), 5.0(s,2H), 6.5(s,1H), 7.0–8.0 (complex m,23H); mass spectrum (+ve FAB, DMSO): 699 (M+H)$^+$.

EXAMPLE 7

Using an analogous procedure to that described in Example 6, but starting from the appropriate compound of formula III, wherein L is triphenylmethyl, there was obtained 2,6-dimethyl-3-(1-imidazolylmethyl)-4-[2'-(1H-tetrazol-5-yl)biphenyl-4-yl)methoxy]pyridine dihydrochloride as a solid (75% yield), m.p. 125°–127° C.; NMR (d$_6$-DMSO/d$_4$-acetic acid): 2.7(s,3H), 2.9(s,3H), 5.4(s,2H), 5.55(s,2H), 7.1–7.8 (complex m,11H), 8.9(s,1H); mass spectrum (+ve FAB, DMSO): 438 (M+H)$^+$; microanalysis, found: C,54.2; H,5.4; N,16.6; H$_2$O,6.1%; C$_{25}$H$_{23}$N$_7$O.2HCl.2H$_2$O requires: C,54.9; H,5.3; N,17.9%.

The necessary starting material of formula III, corresponding to starting material D in Example 6, was obtained as follows:

Sodium hydride (60% dispersion in mineral oil; 37 mg) was added to a solution of imidazole (110 mg) in DMF (20 ml) and the solution was stirred at 50° C. for 10 minutes. 3-Chloromethyl-2,6-dimethyl-4-[(2'-triphenylmethyl-2H-tetrazol-5-yl)biphenyl-4-yl)-methoxy]pyridine (1.0 g) (obtained as described in Example 6, part (iii)) was added and the mixture was stirred at ambient temperature for 16 hours. Solvent was removed by evaporation and the residue dissolved in dichloromethane washed with water, saturated sodium chloride solution and dried (MgSO$_4$). Solvent was removed by evaporation and the residue purified by flash chromatography eluting with dichloromethane/methanol (19:1 v/v) increasing to (10:1 v/v) to give 2,6-dimethyl-3-(1-imidazolylmethyl)-4-[(2'-(2-triphenylmethyl-2H-tetrazol-5-yl)biphenyl-4-yl)methoxy]pyridine (1.08 g); NMR (d$_6$-DMSO/d$_4$-acetic acid): 2.45(s,3H), 2.5(s,3H), 5.2(2s,4H), 6.8–8.1 (complex m,27H); mass spectrum (d$_6$-DMSO): 680 (M$_+$H)$^+$.

EXAMPLE 8

Using analogous procedure to that described in Example 1, but starting from the appropriate compound of formula III wherein L is triphenylmethyl, there was thus obtained 3-benzoyl-6-ethyl-2-methyl-4-[(2'-(1H-tetrazol-5-yl)biphenyl-4-yl)methoxy]pyridine hydrochloride as a solid (89% yield), m.p. 211°–217° C.; NMR (d$_6$-DMSO/d$_4$-acetic acid); 1.39(t, 3H), 2.49(s, 3H), 3.00(q, 2H), 5.38(s, 2H), 6.87–6.99(m, 4H), 7.26–7.86-(complex m, 10H); mass spectrum (+ve FAB, methanol/nitrobenzyl alcohol): 498(M+Na)$^+$, 476(M+H)$^+$; microanalysis, found: C,68.2; H,4.9; N,13.3%; C$_{29}$H$_{25}$N$_5$O$_2$.HCl requires: C,68.0; H,5.1; N,13.7%.

The necessary starting material of formula III corresponding to starting material A in Example 1, was obtained in a yield of 63% using an analogous procedure to that described in Example 1, part (iii), as follows:

EXAMPLE 8A 3-benzoyl-6-ethyl-2-methyl-[(2'-(2-triphenylmethyl-2H-tetrazol-5-yl)biphenyl-4-yl)methoxy]pyridine as a solid, m.p. 92° C.; NMR (CDCl$_3$): 1.31(t, 3H), 2.39(s, 3H), 2.79(q, 2H), 4.91(s, 2H), 6.64–6.83(m, 3H), 6.83–6.98(complex m, 8H), 7.14–7.61(complex m, 15H), 7.81–7.93(complex m, 3H); mass spectrum (+ve FAB, methanol/nitrobenzyl alcohol): 740(M+Na)$^+$, 718(M+H)$^+$.

The necessary starting material of formula IV, corresponding to compound B in Example 1, was obtained as follows:

A mixture of 3-amino-1-phenyl-2-buten-1-one (2.3 g) and 5-(1-hydroxypropylidene)-2,2-dimethyl-1,3-dioxane-4,6-dione (4.0 g) was heated at 120° C. for 1 hour. The mixture was cooled to ambient temperature and the residue was purified by flash chromatography eluting with dichloromethane/methanol (19:1 v/v) to give 3-benzoyl-1,4-dihydro-6-ethyl-2-methyl-4-oxopyridine (0.95 g) as a solid, m.p. 203° C.; NMR (d$_6$-DMSO): 1.2(t, 3H), 2.07(s, 3H), 2.5(q, 2H), 5.96(s, 1H), 7.44–7.50(m, 2H), 7.57–7.60(m, 1H), 7.72–7.76(m, 2H), 11.3(broad s, 1H); mass spectrum (chemical ionisation, ammonia): 242(M+H)$^+$.

EXAMPLE 9

Concentrated hydrochloric acid (0.2 ml) was added to a solution of 2,6-dimethyl-3-(pyrimidin-5-yl)-4-[(2'-(2-triphenylmethyl-2H-tetrazol-5-yl)biphenyl-4-yl)methoxy]pyridine (A) (0.3 g) in methanol (15 ml) and the mixture was stirred for 1 hour. Volatile material was removed by evaporation and the residue was purified by flash chromatography eluting with dichloromethane/methanol/trifluoroacetic acid (85:15:1 v/v/v) to give 2,6-dimethyl-3-(pyrimidin-5-yl)-4-[(2'-(1H-tetrazol-5-yl)biphenyl-4-yl)methoxy]pyridine trifluoroacetate as a solid, m.p. 225°°C.; NMR (d$_6$-DMSO): 2.37(s, 3H), 2.65(s, 3H), 5.33(s, 2H), 7.07(d, 2H), 7.21(d, 2H), 7.62(m, 5H), 8.87(s, 2H), 9.23(s, 1H); mass spectrum (+ve FAB, methanol/nitrobenzyl alcohol): 436(M+H)$^+$, microanalysis, found: C, 44.1; H, 3.0; N, 11.4%; C$_{25}$H$_{21}$N$_7$0.3.5(CF$_3$CO$_2$H).H$_2$O requires: C, 45.0; H, 3.1; N, 11.5%.

The starting material A was obtained as follows:
(i) 1,4-Dihydro-2,6-dimethyl-3-iodo-4-oxopyridine (6.5 g) (obtained as described in Chem. Pharm. Bull., 1986, 34, 2719) was added to a stirred suspension of sodium hydride (oil free, 1.04 g) in DMF (35 ml). When evolution of hydrogen ceased benzyl chloride (3.3 g) was added. The mixture was heated at 50° C. for 3 hours and then left to stand for 30 hours. The mixture was added to water (150 ml) and the resultant precipitate collected by filtration to give 2,6-dimethyl-3-iodo-4-(phenylmethoxy)pyridine (B) (5.7 g), m.p. 68°–70° C.; NMR (CDCl$_3$): 2.45(s, 3H), 2.75(s, 3H), 5.2(s, 2H), 6.45(s, 1H), 7.35–7.45(m, 5H).

(ii) 5-(Tributylstannyl)pyrimidine (0.6 g) (obtained as described in Chem. Abs., 1979, 91 (17), 140997 starting from 5-bromopyrimidine and tributyltin chloride) was added to a solution of compound B (0.34 g) and tetrakis(triphenylphosphine)palladium (O) (60 mg) in DMF (10 ml). The mixture was stirred at 150° C. under an argon atmosphere for 16 hours. The mixture was cooled to ambient temperature and volatile material was removed by evaporation. The residue was partitioned between water and ethyl acetate. The organic phase was separated and the aqueous phase was extracted with ethyl acetate. The combined organic phases were dried (MgSO$_4$) and solvent was removed by evaporation. The residue was purified by flash chromatography eluting with ethyl acetate/methanol (9:1 v/v) to give 2,6-dimethyl-4-(phenylmethoxy)-3-(pyrimidin-5-yl)pyridine (C) (0.18 g) as a solid, m.p. 119°–120° C.; NMR (CDCl$_3$): 2.35(s, 3H), 2.56(s, 3H), 5.08(s, 2H), 6.72(s, 1H), 7.20(m, 2H), 7.30(m, 3H), 9.20(s, 1H); mass spectrum (chemical ionisation, ammonia): 292(M+H)$^+$.

(iii) A solution of compound C (0.4 g) in ethanol (20 ml) was catalytically hydrogenated over 10% palladium on carbon at 1 atmosphere pressure for 24 hours. Catalyst was removed by filtration and solvent was removed from the filtrate by evaporation to give 1,4-dihydro-2,6-dimethyl-4-oxo-3-(pyrimidin-5-yl)pyridine (D) (0.22 g) as a solid; NMR (d$_6$-DMSO): 2.15(s, 3H), 2.22(s, 3H), 6.00(s, 1H), 8.64(s, 2H), 9.06(s, 1H), 11.30(broad s, 1H); mass spectrum (chemical ionisation, ammonia): 202(M+H)$^+$.

(iv) Compound D (0.2 g) was added to a suspension of sodium hydride (60% dispersion in mineral oil; 40 mg) in DMF (10 ml) and the mixture was stirred for 30 minutes. 5-[2-(4'-Bromomethylbiphenylyl]-2-triphenylmethyl-2H-tetrazole (0.56 g) was added and the mixture was stirred for 16 hours. Solvent was removed by evaporation and the residue was purified by flash chromatography to give 2,6-dimethyl-3-(pyrimidin-5-yl)-4-[(2'-(2-triphenylmethyl-2H-tetrazol-5-yl)biphenyl-4-yl)methoxy]pyridine (A) (0.37 g) as a solid, m.p. 171°–172° C.; NMR (CDCl$_3$): 2.35(s, 3H), 2.52(s, 3H), 4.96(s, 2H), 6.68(s, 1H), 6.91(complex m, 8H), 7.0(d, 2H), 7.23(complex m, 10H), 7.47(m, 2H), 7.93(m, 1H), 8.68(s, 2H), 9.2(s, 1H).

EXAMPLES 10–12

Using an analogous procedure to that described in Example 9 but starting from the appropriate compound of formula III wherein L is triphenylmethyl, the following compounds of formula I were obtained in yields of 54–85%:

EXAMPLE 10

2,6-dimethyl-3-(2-methoxypyridin-5-yl)-4-[(2'-(1H-tetrazol-5-yl)biphenyl-4-yl)methoxy]pyridine hydrochloride as a solid, m.p. 120°–121° C. (decomposition); NMR (d$_6$-DMSO): 2.21(s, 3H), 2.43(s, 3H), 3.88(s, 3H), 5.13(s, 2H), 6.6(d, 1H), 6.97(s, 1H), 7.05(d, 2H), 7.18(d, 2H), 7.6(m, 5H), 8.04(d, 1H); mass spectrum (+ve FAB): 465(M+H)$^+$; high resolution mass spectrum, found: 465.2034; C$_{27}$H$_{24}$N$_6$O$_2$.H requires: 465.2039.

EXAMPLE 11

2,6-dimethyl-3-(4-ethoxycarbonylphenyl)-4-[(2'-(1H-tetrazol-5-yl)biphenyl-4-yl)methoxy]pyridine as a solid, m.p. 196°–197° C.; NMR ($d_6$-DMSO): 1.34(t, 3H), 2.15(s, 3H), 2.43(s, 3H), 4.33(q, 2H), 5.12(s, 2H), 6.97(s, 1H), 7.02(d, 2H), 7.13(d, 2H), 7.40(d, 2H), 7.50(m, 4H), 8.0(d, 2H); mass spectrum (+ve FAB, DMSO/nitrobenzyl alcohol): 506(M+H)$^+$; microanalysis, found: C, 70.1; H, 5.3; N, 13.8%; $C_{30}H_{37}N_5O_3.0.5H_2O$ requires: C, 70.0; H, 5.4; N, 13.6%.

EXAMPLE 12

2,6-dimethyl-3-(3-ethoxycarbonylphenyl)-4-[(2'-(1H-tetrazol-5-yl)biphenyl-4-yl)methoxy]pyridine as a solid, m.p. 200°–201° C. (decomposition); NMR ($d_6$-DMSO): 1.3(t, 3H), 2.17(s, 3H), 2.44(s, 3H), 4.3(q, 2H), 5.12(s, 2H), 6.97(s, 1H), 7.0(d, 2H), 7.14(d, 2H), 7.52(m, 6H), 7.84(m, 1H), 7.93(m, 1H); mass spectrum (+ve FAB, methanol/nitrobenzyl alcohol): 506(M+H)$^+$, microanalysis, found: C, 67.5; H, 5.4; N, 13.1%; $C_{30}H_{27}N_5O_3.HCl.1.5H_2O$ requires: C, 67.6; H, 5.6; N, 13.1%.

The necessary starting materials of formula III used in Examples 10–12, corresponding to starting material A in Example 9, were obtained in yields of 53–77% using an analogous procedure to that described in Example 9, part (iv), as follows:

EXAMPLE 10A 2,6-dimethyl-3-(2-methoxypyridin-5-yl)-4-[(2'-(2-triphenylmethyl-2H-tetrazol-5-yl)biphenyl-4-yl)methoxy]pyridine as a solid, m.p. 130°–131° C.; NMR (CDCl$_3$): 2.38(s, 3H), 2.54(s, 3H), 4.01(s, 3H), 4.99(d, 2H), 6.69(s, 1H), 6.96(complex m, 8H), 7.12(d, 2H), 7.27(complex m, 11H), 7.50(m, 3H), 7.97(m, 1H), 8.14(m, 1H).

EXAMPLE 11A 2,6-dimethyl-3-(4-ethoxycarbonylphenyl)-4-[(2'-(2-triphenylmethyl-2H-tetrazol-5-yl)biphenyl-4-yl)methoxy]pyridine as a foam; NMR (CDCl$_3$): 1.4(t, 3H), 2.29(s, 3H), 2.51(s, 3H), 4.38(q, 2H), 4.93(s, 2H), 6.61(s, 1H), 6.88(complex m, 8H), 7.03(d, 2H), 7.2(complex m, 9H), 7.35(m, 4H), 7.45(M, 2H), 7.92(m, 1H), 8.12(d, 2H).

EXAMPLE 12A 2,6-dimethyl-3-(3-ethoxycarbonylphenyl)-4-[(2'-(2-triphenylmethyl-2H-tetrazol-5-yl)biphenyl-4-yl)methoxy]pyridine as a solid; NMR (CDCl3): 1.36(t, 3H), 2.31(s, 3H), 2.51(s, 3H), 4.36(q, 2H), 4.94(s, 2H), 6.64(s, 1H), 6.9(complex m, 9H), 7.02(d, 2H), 7.26(complex m, 9H), 7.46(m, 4H), 7.9(m, 1H), 8.01(m, 2H).

The necessary starting materials used in Examples 10–12 corresponding to compound C in Example 9 were obtained in yields of 27–78% using an analogous procedure to that described in Example 9, part (ii), as follows:

EXAMPLE 10C 2,6-dimethyl-3-(2-methoxypyridin-5-yl)-4-(phenylmethoxy)pyridine as an oil; NMR (CDCl$_3$): 2.32(s, 3H), 2.51(s, 3H), 3.98(s, 3H), 5.06(s, 2H), 6.63(s, 1H), 7.3(m, 3H), 7.5(m, 3H), 7.68(m, 1H), 8.08(d, 1H); mass spectrum (chemical ionisation, ammonia): 321(M+H)$^+$; starting from 2-methoxy-5-(tributystannyl)pyridine, itself obtained using the procedure described in Chem. Abs. 1979, 91 (17), 140997 but starting from 5-bromo-2-methoxypyridine and tributyltin chloride.

EXAMPLE 11C 2,6-dimethyl-3-(4-ethoxycarbonylphenyl)-4-(phenylmethoxy)pyridine as an oil; NMR (CDCl$_3$): 1.4(t, 3H), 2.31(s, 3H), 2.60(s, 3H), 4.41(q, 2H), 5.1(s, 2H), 6.7(s, 1H), 7.15(m, 2H), 7.26(m, 5H), 8.1(d, 2H); mass spectrum (chemical ionisation, ammonia) 362(M+H)$^+$; starting from ethyl (4-tributylstannyl)benzoate, itself obtained as described in J. Org. Met. Chem., 1989, 367, 259.

EXAMPLE 12C 2,6-dimethyl-3-(3-ethoxycarbonylphenyl)-4-(phenylmethoxy)pyridine as an oil; NMR (CKCl$_3$): 1.39(t,3H), 2.30(s,3H), 2.53(s,3H), 4.38(q,2H), 5.06(s,2H), 6.67(s,1H), 7.12(m,2H), 7.27(m,3H), 7.48(m,2H), 8.0(m,2H); mass spectrum (chemical ionisation, ammonia): 362(M+H)$^+$; starting from ethyl (3-tributylstannyl)benzoate, itself obtained using the procedure described in J. Org. Met. Chem., 1989, 367, 259 but starting from ethyl 3-iodobenzoate.

The necessary starting materials of formula IV used in Examples 10–12, corresponding to compound D in Example 9, were obtained in yields of 66–77% using an analogous procedure to that described in Example 9, part (iii), as follows:

EXAMPLE 10D 1,4-dihydro-2,6-dimethyl-3-(2-methoxypyridin-5-yl)-4-oxopyridine as a solid, m.p. 238°–240° C.; NMR ($d_6$-DMSO): 2.09(s, 3H), 2.20(s, 3H), 3.86(s, 3H), 5.94(s, 1H), 6.80(d, 1H), 7.5(d, 1H), 7.92(d, 1H),11.18(broad s, 1H); mass spectrum (chemical ionisation, ammonia): 231(M+H)$^+$.

EXAMPLE 11D 1,4-dihydro-2,6-dimethyl-3-(4-ethoxycarbonylphenyl)-4-oxopyridine as a solid; NMR ($d_6$-DMSO): 1.33(t, 3H), 2.06(s, 3H), 2.21(s, 3H). 4.32(q, 2H), 5.98(s, 1H), 7.31(d, 2H), 7.93(d, 2H), 11.2(broad s, 1H); mass spectrum (chemical ionisation, ammonia): 272(M+H)$^+$.

EXAMPLE 12D 1,4-dihydro-2,6-dimethyl-3-(3-ethoxycarbonylphenyl)-4-oxopyridine as a solid, m.p. 228°–229° C.; NMR($d_6$-DMSO): 1.32(t,3H), 2.04(3,3H), 2.20(s,3H), 4.31(q,2H), 5.95(s,1H), 7.46(m,2H), 7.74(s,1H), 7.86(d,2H); mass spectrum (chemical ionisation, ammonia): 272(M+H)$^+$.

EXAMPLE 13

Using an analogous procedure to that described in Example 9, but starting from the appropriate compound of formula III wherein L is triphenylmethyl, there was obtained 2,6-diethyl-3-(4-ethoxycarbonylphenyl)-4-[(2'-(1H-tetrazol-5-yl)biphenyl-4-yl)methoxy]pyridine as a solid (in 85% yield), m.p. 107°–110° C. (decomposition); NMR ($d_6$-DMSO): 1.02(t, 3H), 1.25(t, 3H), 1.34(t, 3H), 2.41(q, 2H), 2.71(q, 2H), 4.33(q, 2H), 5.12(s, 2H), 6.94(s, 1H), 7.01(d, 2H), 7.13(d, 2H), 7.39(d, 2H), 7.51(m, 4H), 8.0(d, 2H); mass spectrum (+ve FAB, DMSO/nitrobenzyl alcohol): 534(M+H)$^+$; microanalysis, found: C, 69.8; H, 5.9; N, 12.7%; $C_{32}H_{31}N_5O_3.0.75H_2O$ requires: C, 70.2; H, 5.9; N, 12.8%.

The necessary starting material of formula III used in Example 13 corresponding to starting material A in Example 9 was obtained in 42% yield using an analogous procedure to that described in Example 9, part (iv), as follows:

EXAMPLE 13A 2,6-diethyl-3-(4-ethoxycarbonylphenyl)-4-[2'-(2-triphenylmethyl-2H-tetrazol-5-yl)biphenyl-4-yl)methoxy]pyridine as a foam; NMR (CDCl$_3$): 1.11(t, 3H), 1.29(t, 3H), 1.36(t, 3H), 2.91(q, 2H), 2.57(q, 2H), 4.40(q, 2H), 4.96(s, 2H), 6.64(s, 1H), 6.89(m, 2H), 7.27(complex m, 14H), 7.46(m, 2H), 7.91(m, 1H), 8.12(m, 2H); mass spectrum (+ve FAB): 776(M+H)$^+$, starting from 2,6-diethyl-1,4-dihydro-3-(4-ethoxycarbonylphenyl)-4-oxopyridine, itself obtained as follows:

(i) 2M Sodium hydroxide (30 ml) was added to a solution of methyl 2,6-diethyl-1,4-dihydro-4-oxopyridine-3-carboxylate (obtained as described in European Patent Application No. 453210) in methanol (60 ml) and the solution was heated under reflux for 48 hours. Volatile material was removed by evaporation and the residue was dissolved in water (50 ml). The solution was washed with ethyl acetate and acidified to pH 4 with 1M citric acid solution. The resultant precipitate was collected by filtration to give 2,6-diethyl-1,4-dihydro-4-oxopyridine-3-carboxylic acid (E) (2.1 g), m.p. 238°–240° C. (decomposition); NMR (CDCl$_3$): 1.3(t, 6H), 2.7(q, 2H), 3.3(q, 2H), 6.45(s, 1H), 12.1(br s, 1H).

(ii) Compound E (1.0 g) was heated at 250° C. in a sublimation apparatus. The sublimation was collected and purified by flash chromatography, eluting with methanol/dichloromethane (1:9 v/v), to give 2,6-diethyl-4(1H)-pyridone (F) (0.58 g), m.p. 103°–110° C.; NMR (CDCl$_3$): 1.3(t, 6H), 2.7(q, 4H), 6.2(s, 2H), 12.3–13.0(br s, 1H).

(iii) Iodine (720 mg) was added to a solution of compound F (430 mg) and sodium hydroxide (120 mg) in water (15 ml) and the mixture was stirred for 1 hour. The precipitated solid was collected by filtration and purified by flash chromatography, eluting with methanol/dichloromethane (1:19 v/v), to give 2,6-diethyl-3-iodo-4(1H)-pyridone (G) (290 mg), m.p. 225°–227° C.; NMR (d$_6$-DMSO): 1.15(t, 6H), 2.5(q, 2H), 2.8(q, 2H), 5.9(s, 1H), 11.4(br s, 1H).

(iv) Using an analogous procedure to that described in Example 9, part (i) but starting from compound G, there was obtained in 63% yield 2,6-diethyl-3-iodo-4-(phenylmethoxy)pyridine (H) as an oil; NMR (CDCl$_3$): 1.26(t, 6H), 2.72(q, 2H), 3.03(q, 2H), 5.19(s, 2H), 6.45(s, 1H), 7.39(m, 5H).

(v) Using an analogous procedure to that described in Example 9, part (ii) but starting from compound H, there was obtained in 59% yield 2,6-diethyl-3-(4-ethoxycarbonylphenyl)-4-(phenylmethoxy)pyridine (I) as an oil; NMR (CDCl$_3$): 1.30(t, 3H), 1.42(t, 3H), 2.55(q, 2H), 2.80(q, 2H), 4.40(q, 2H), 5.09(s, 2H), 6.65(s, 1H), 7.16(m, 2H), 7.30(m, 5H), 8.1(d, 2H); mass spectrum (chemical ionisation, ammonia) 390(M+H)$^+$.

(vi) Using an analogous procedure to that described in Example 9, part (iii), but starting from compound I, there was obtained in 84% yield 2,6-diethyl-1,4-dihydro-3-(4-ethoxycarbonylphenyl)-4-oxopyridine as a solid, NMR (d$_6$-DMSO): 0.87,1.07(two t, 3H), 1.21(t, 3H), 1.33(t, 3H), 2.34(t, 3H), 2.53(q, 2H), 4.32(q, 2H), 6.03,6.25(two s, 1H), 7.29(d, 2H), 7.95(d, 2H); mass spectrum (chemical ionisation, ammonia): 300(M+H)$^+$.

EXAMPLE 14

2,6-Dimethyl-3-(4-ethoxycarbonylphenyl)-4-[(2'-(1H-tetrazol-5-yl)biphenyl-4-yl)methoxy]pyridine (50 mg) was added to a mixture of 1M sodium hydroxide solution (0.2 ml) and ethanol (2 ml) and the mixture was heated at reflux for 1 hour. Additional 1M sodium hydroxide solution (0.1 ml) was added and the mixture was heated at reflux for a further 30 minutes. Volatile material was removed by evaporation. The residue was dissolved in water (10 ml) and the mixture was extracted with dichloromethane. The aqueous phase was separated and adjusted to pH 5 with 1M citric acid solution. The resultant precipitate was collected by filtration to give 3-(4-carboxyphenyl)-2,6-dimethyl-4-[(2'-(1H-tetrazol-5-yl)biphenyl-4-yl)methoxy]pyridine as a solid, m.p. 207°–210° C. (decomposition); NMR (d$_6$-DMSO): 2.1(s, 3H), 2.44(s, 3H), 5.13(s, 2H), 6.94(s, 1H), 7.03(d, 2H), 7.15(d, 2H), 7.38(d, 2H), 7.55(m, 4H), 9.8(d, 2H); mass spectrum (+ve FAB, methanol/nitrobenzyl alcohol): 478(M+H)$^+$; microanalysis, found: C, 66.6, H, 5.0; N, 13.9%; C$_{28}$H$_{23}$N$_5$O$_3$.1.5H$_2$O requires: C, 66.7; H, 5.1; N, 13.9%.

EXAMPLES 15–16

Using an analogous procedure to that described in Example 14, the following compounds were obtained in yields of 58–63%:

EXAMPLE 15

3-(3-carboxyphenyl)-2,6-dimethyl-4-[(2'-(1H-tetrazol-5-yl)biphenyl-4-yl)biphenyl-4-yl)methoxy]pyridine as a solid, m.p. 228°–230° C. (decomposition); NMR (d$_6$-DMSO): 2.18(s, 3H), 2.44(s, 3H), 5.13(s, 2H), 6.98(s, 1H), 7.02(d, 2H), 7.15(m, 6H), 7.83(s, 1H), 7.92(m, 1H); microanalysis, found: C, 66.3; H, 5.0; N, 13.5%; C$_{28}$H$_{23}$N$_5$O$_3$.1.5H$_2$O requires: C, 66.6; H, 5.1; N, 13.0%.

EXAMPLE 16

3-(4-carboxyphenyl)-2,6-diethyl-4-[(2'-(1H-tetrazol-5-yl)biphenyl-4-yl)methoxy]pyridine as a solid, m.p. 229°–232° C. (decomposition); NMR (d$_6$-DMSO): 1.03(t, 3H), 1.25(t, 3H), 2.46(q, 2H), 2.72(q, 2H), 5.14(s, 2H), 6.94(s, 1H), 7.02(d, 2H), 7.15(d, 2H), 7.37(d, 2H), 7.59(m, 4H), 7.98(d, 2H); mass spectrum (+ve FAB, DMSO/methanol/nitrobenzyl alcohol): 506(M+H)$^+$; microanalysis, found: C, 69.9; H, 5.5; N, 13.6%; C$_{30}$H$_{27}$N$_5$O$_3$.0.5H$_2$O requires: C, 70.0; H, 5.4; N, 13.6%.

EXAMPLE 17

Using an analogous procedure to that described in Example 9. but starting from the appropriate compound of formula III wherein L is triphenylmethyl, there was obtained 2,6-dimethyl-3-[(4-methoxycarbonylphenyl)-methyl]-4-[(2'-(1H-tetrazol-5-yl)biphenyl-4-yl)methoxy]pyridine as a solid (in 45% yield), m.p. 144°–145° C.; NMR (d$_6$-DMSO): 2.36(s, 3H), 2.40(s, 3H), 3.79(s, 3H), 5.17(s, 2H), 6.95(s, 1H), 7.05(d, 2H), 7.23(d, 2H), 7.38(m, 2H), 7.67(m, 6H); mass spectrum (+ve FAB, DMSO/methanol/nitrobenzyl alcohol): 506(M+H)$^+$; microanalysis, found: C, 69.2; H, 5.4; N, 13.6%; C$_{30}$H$_{27}$N$_5$O$_3$.0.75H$_2$O requires: C, 69.3; H, 5.5; N, 13.5%.

The necessary starting material of formula III used in Example 17 corresponding to starting material A in Example 9 was obtained in 65% yield using an analogous procedure to that described in Example 9, part (iv), as follows:

EXAMPLE 17A 2,6-dimethyl-3-[(4-methoxycarbonylphenyl)methyl]-4-[(2'-(2-triphenylmethyl-2H-tetrazol-5-yl)biphenyl-4-yl)methoxy]pyridine (A) as a foam; NMR (CDCl$_3$): 2.48(double s, 6H), 3.84(s, 3H), 4.96(s, 2H), 6.62(s, 1H), 6.91(m, 6H), 7.02(d, 2H), 7.08(d, 2H), 7.27(complex m, 11H), 7.37(m, 1H), 7.46(m, 2H), 7.83(m, 2H), 7.92(m, 1H), starting from 1,4-dihydro-2,6-dimethyl-3-[(4-methoxycarbonylphenyl)methyl]-4-oxopyridine, itself obtained as follows:

(i) Methyl 4-(bromomethyl)benzoate (1.15 g) was added to a stirred suspension of zinc dust (0.49 g) in THF (15 ml) and the mixture was stirred for 2 hours. A solution of 2,6-dimethyl-3-iodo-4-(phenylmethoxy)pyridine (0.5 g) in THF (10 ml) and tetrakis(triphenylphosphine)palladium (O) (87 mg) was added to the mixture. The mixture was heated at reflux for 2 hours and then cooled to ambient temperature. The mixture was filtered and solvent was removed from the filtrate by evaporation. The residue was partitioned between ethyl acetate and a solution of ethylene diaminetetracetic acid. The organic phase was separated and washed with saturated sodium chloride solution and dried (MgSO$_4$). Solvent was removed by evaporation and the residue was purified by flash chromatography, eluting with ethyl acetate, to give 2,6-dimethyl-3-[(4-methoxycarbonylphenyl)methyl]-4-(phenylmethoxy)pyridine (A) as an oil; NMR (CDCl$_3$): 2.5(d of s, 6H), 3.88(s, 3H), 4.07(s, 2H), 5.09(s, 2H), 6.63(s, 1H), 7.28(complex m, 7H), 7.83(m, 2H); mass spectrum (chemical ionisation, ammonia): 362(M+H)$^+$.

(ii) Using an analogous procedure to that described in Example 9, part (iii) but starting from compound B, there was obtained in 86% yield 1,4-dihydro-2,6-dimethyl-3-[(4-methoxycarbonylphenyl)methyl]4-oxopyridine as a solid, m.p. 226°-228° C.; NMR (d6-DMSO): 2.14(d of s, 6H), 3.79(s, 2H), 3.81(s, 3H), 5.88(s, 1H), 7.4(m, 3H), 7.63(d, 2H), 10.94(s, 1H); mass spectrum (chemical ionisation, ammonia): 272(M+H)$^+$.

EXAMPLE 18 (Note: all parts by weight)

The compounds of the invention may be administered for therapeutic or prophylactic use to warm-blooded animals such as man in the form of conventional pharmaceutical compositions, typical examples of which include the following:

| | |
|---|---|
| a) Capsule (for oral administration) | |
| Active ingredient * | 20 |
| Lactose powder | 578.5 |
| Magnesium stearate | 1.5 |
| b) Tablet (for oral administration) | |
| Active ingredient * | 50 |
| Microcrystalline cellulose | 400 |
| Starch (pregelatinised) | 47.5 |
| Magnesium stearate | 2.5 |
| c) Injectable Solution (for intravenous administration) | |
| Active ingredient * | 0.05-1.0 |
| Propylene glycol | 5.0 |
| Polyethylene glycol (300) | 3.0-5.0 |
| Purified water | to 100% |
| d) Injectable Suspension (for intramuscular administration) | |
| Active ingredient * | 0.05-1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

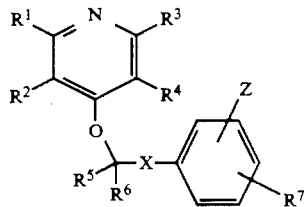

I

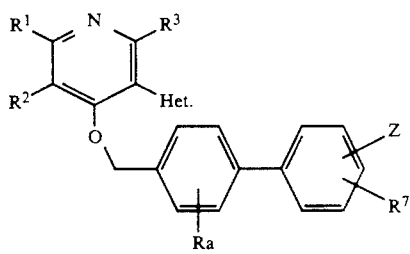

Ia

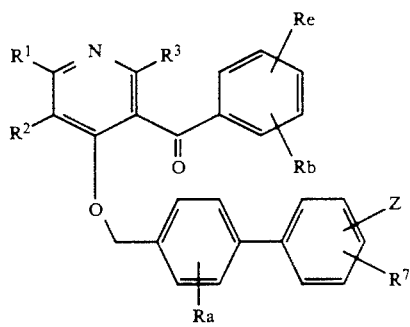

Ib

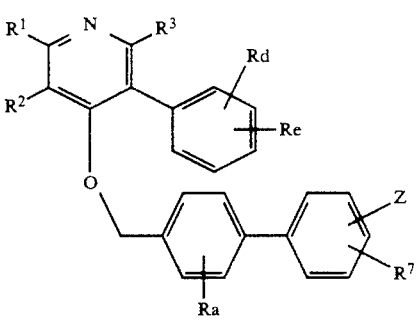

Ic

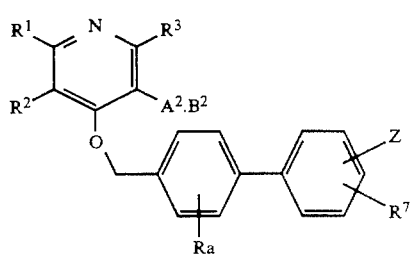

Id

-continued
Chemical Formulae
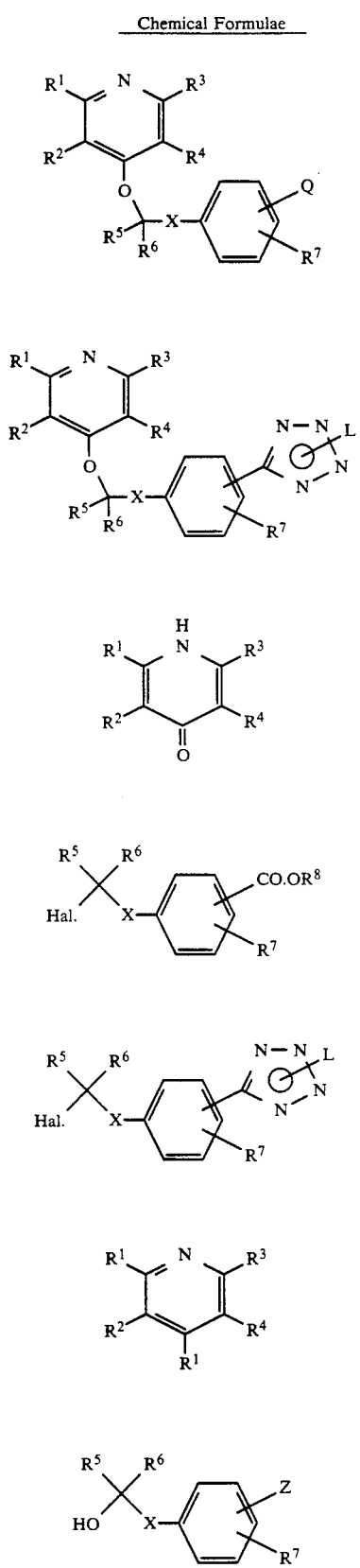
II
III
IV
V
VI
VII
VIII
-continued
Chemical Formulae
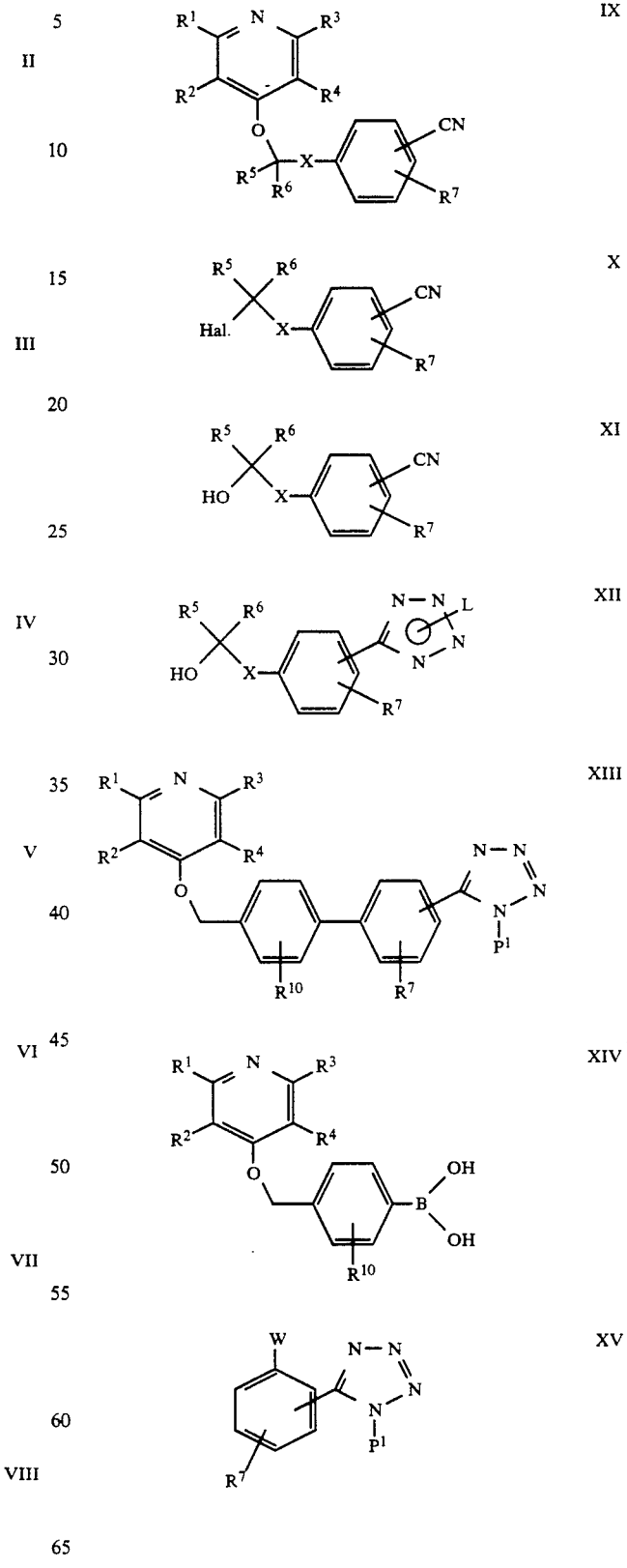
IX
X
XI
XII
XIII
XIV
XV Scheme 1
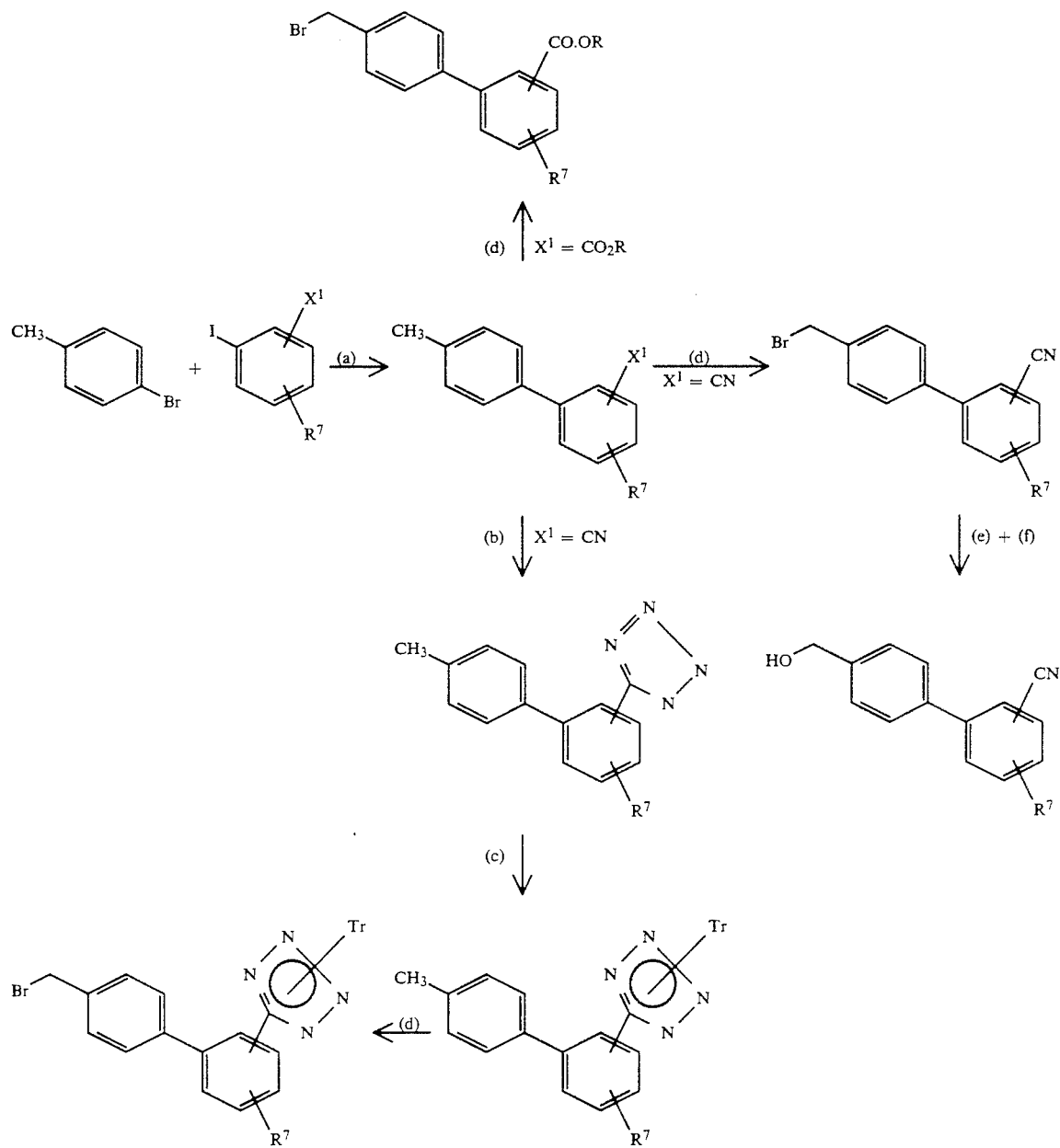
Note:
R = lower alkyl, benzyl, phenyl; Tr = triphenylmethyl (trityl)
Reagents:
a) BuLi/THF; $ZnCl_2/Et_2O$; $Pd(Ph_3P)_4$
b) $Bu_3Sn.N_3$/toulene; HCl/toluene
c) $Tr.Cl/Et_3N/CH_2Cl_2$
d) N-bromosuccinimide/azoisobutyronitrile/$CCl_4$
e) Potassium acetate, hexaoxacyclooctadecane, DME, reflux
f) Lithium borohydride, THF, 0–25° C.

Scheme 2
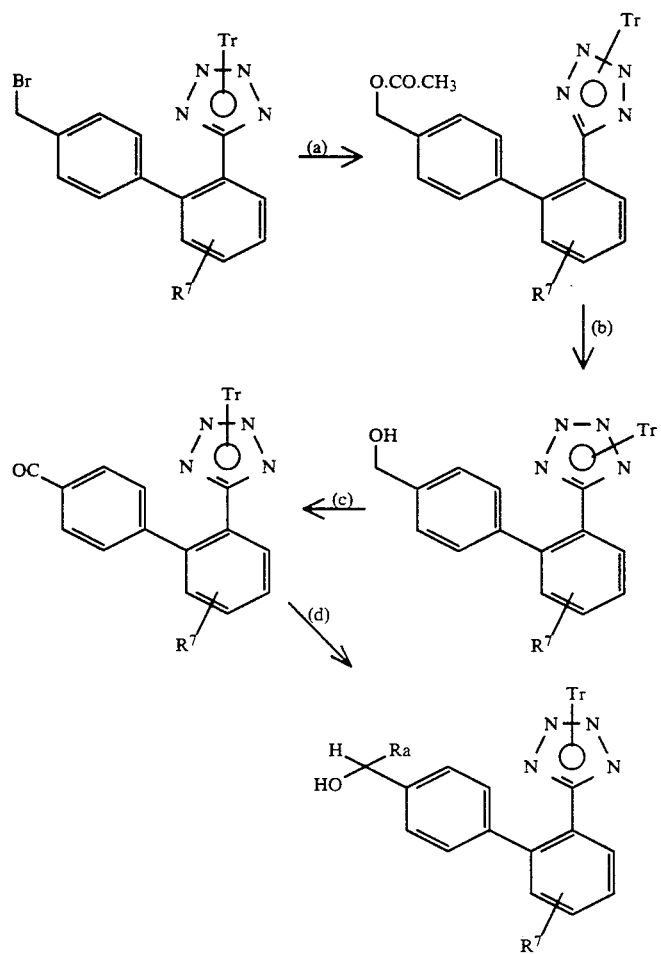
Note
Tr = triphenylmehtyl (trityl)
Ra = (1-4C)alkyl
Reagents:
(a) Potassium acetate, hexaoxacyclooctadecane, DME, reflux
(b) Lithium borohydride, THF, 0-25° C.
(c) Pyridine-SO₃ complex, Et₃N, DMSO, ambient temperature
(d) Ra.M, Et₂O/THF, −50° C. to ambient temperature
Scheme 3
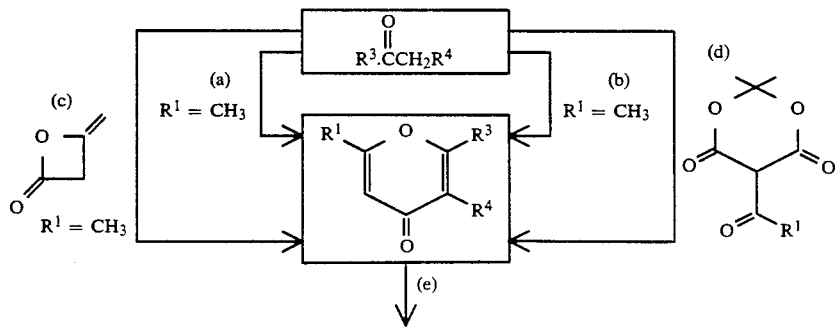

-continued
Scheme 3
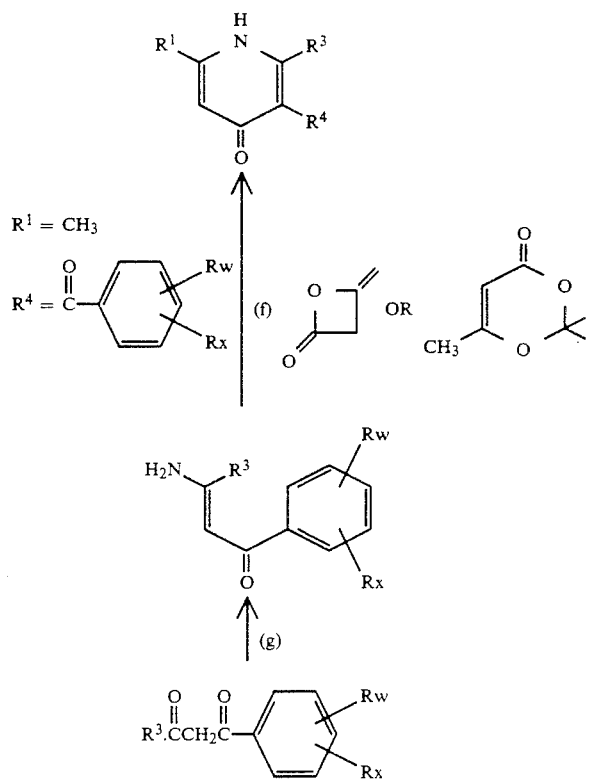
Note:
Rw and Rx are optional substituents
Reagents:
(a) polyphosphoric acid, acetic acid
(b) (i) boron trifluoride, acetic anhydride
   (ii) NaH or (isopropyl)$_2$NLi, ethyl acetate
   (iii) benzene, PTSA, heat or conc. H$_2$SO$_4$, ambient temp.
(c) acetic acid, 0–50° C.
(d) heat, 120° C.
(e) ethanolic ammonia, 120° C., sealed tube
(f) heat
(g) ethanolic ammonia
Scheme 4
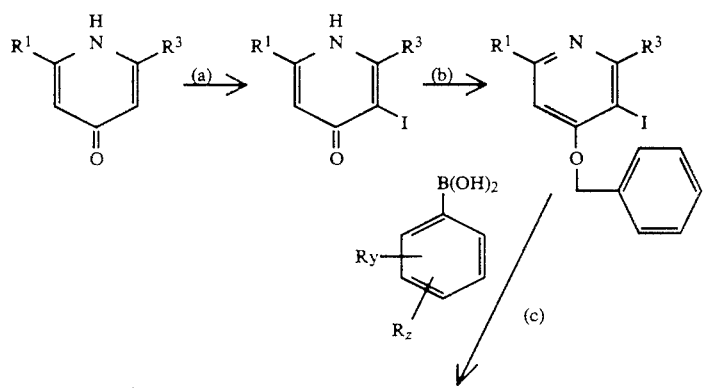

Scheme 4

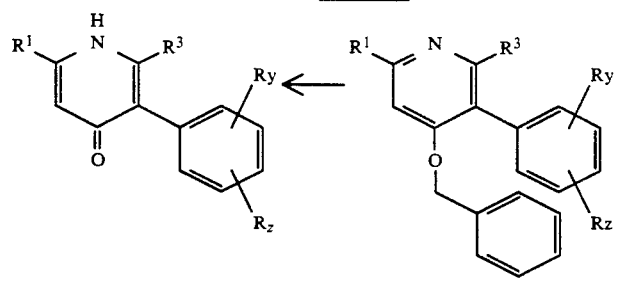

Note:
Ry and Rz are optional substituents
Reagents:
(a) iodine monochloride
(b) benzyl bromide, potassium carbonate, DMF
(c) tetrakis(triphenylphenylphosphine)palladium, triethylamine, dimethoxyethane
(d) hydrogenation, palladium on carbon

Scheme 5

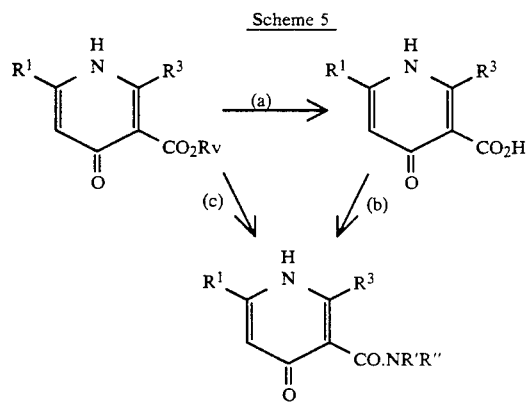

Note:
R' and R" together with the nitrogen atom to which they are attached complete a heterocyclic ring; Rv = lower alkyl
Reagents:
(a) NaOH, ethanol, heat
(b) ethylchloroformate, triethylamine, chloroform
(c) trimethylaluminium, HNR'R", toluene, reflux

Scheme 6

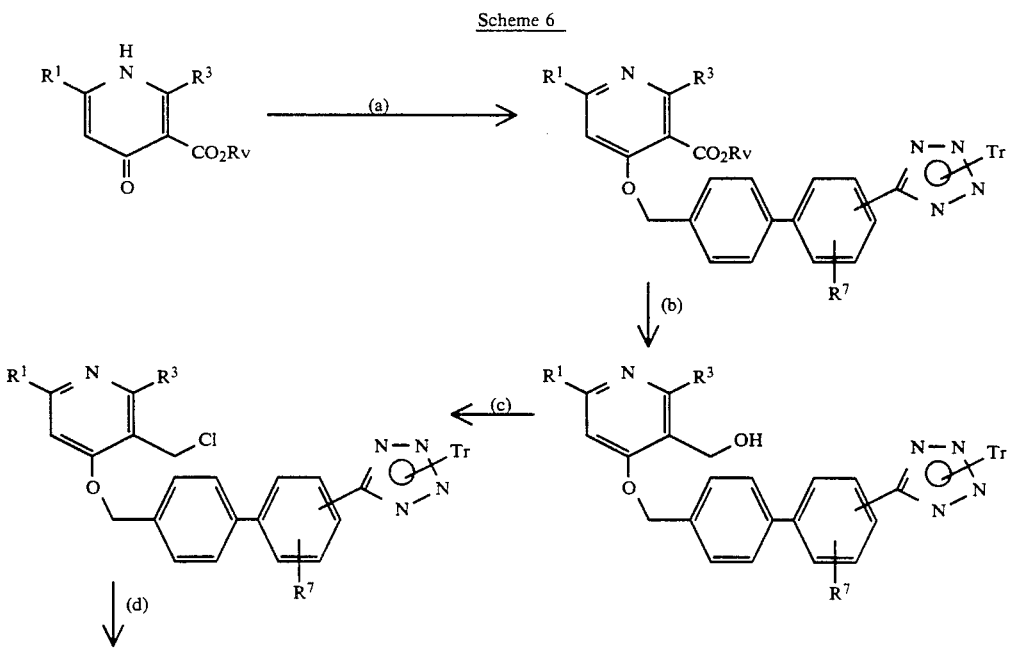

-continued
Scheme 6

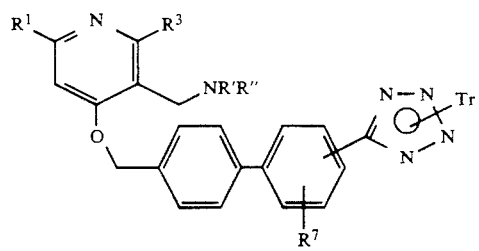

Note:
R' and R" together with the nitrogen atom to which they are attached complete a heterocyclic ring;
Tr = triphenylmethyl
Reagents:
(a) NaH, formula VI compound ($R^5$ and $R^6$ both hydrogen), DMF
(b) lithium borohydride, THF, 0° C.
(c) methanesulphonyl chloride, triethylamine, ambient temperature
(d) HNR'R", $Et_3N/CH_2Cl_2$ or NaH/DMF, 0-50° C.

Scheme 7

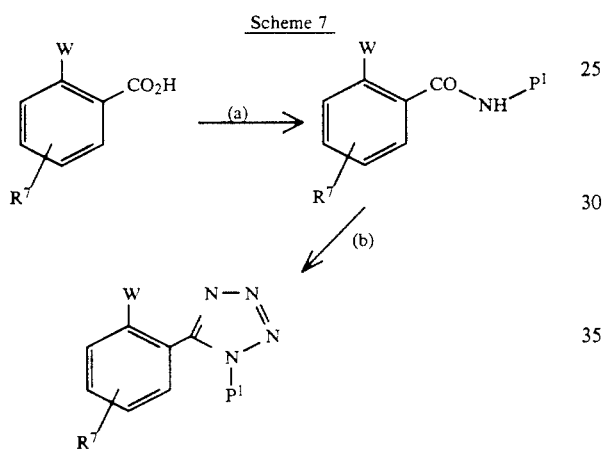

Reagents:
(a) thionyl chloride, DMF, toluene, 80° C.;
then add to $P^1.NH_2$, toluene, NMP, ambient temperature
(b) (i) triethylamine, acetonitrile, DMF;
(ii) thionyl chloride, 10° C.; and
(iii) triethylamine, sodium azide, tetrabutylammonium bromide, 10° C. to ambient temperature

What we claim is:
1. A pyridine compound of the formula I

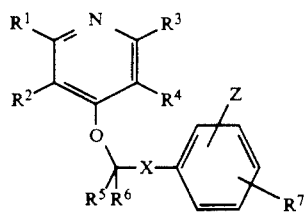

wherein $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, (1-4C)alkoxy or phenyl substituent;
$R^2$ is hydrogen, (1-8C)alkyl, (3-8C)cycloalkyl, (3-8C)cycloalkyl-(1-4C)alkyl, carboxy, (1-4C)alkoxycarbonyl, (3-6C)alkenyloxycarbonyl, cyano, nitro, phenyl or phenyl(1-4C)alkyl; $R^3$ is selected from halogeno, (1-4C)alkoxy, amino, alkylamino and dialkylamino of up to 6 carbon atoms, and any of the values defined for $R^1$;
$R^4$ is a benzoyl group, the phenyl group of which is unsubstituted or bears one or two substituents independently selected from (1-4C)alkyl, (1-4C)alkoxy, halogeno, cyano, trifluoromethyl, nitro, hydroxy, carboxy, (1-4C)alkanoylamino, (1-4C)alkanoyl, fluoro(1-4C)alkoxy, hydroxy(1-4C)alkyl, (1-4C)alkoxy(1-4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1-4C)alkoxycarbonyl, (1-4C)alkanesulphonamido, (1-4C)alkyl.$S(O)_n$-(in which n is zero, 1 or 2), phenyl, phenoxy, benzyloxy, benzyloxycarbonyl, benzamido and benzenesulphonamido, the benzene moiety of the last six groups optionally bearing a halogeno, (1-4C)alkyl or (1-4C)alkoxy substituent;
$R^5$ is hydrogen;
$R^6$ is hydrogen or (1-4C)alkyl;
$R^7$ is selected from hydrogen, (1-4C)alkyl, (1-4C)alkoxy, halogeno, trifluoromethyl, cyano and nitro;
X is phenylene optionally bearing a substituent selected from (1-4C)alkyl, (1-4C)alkoxy, halogeno, trifluoromethyl, cyano and nitro; Z is 1H-tetrazol-5-yl, -CO.NH.(1H-tetrazol-5-yl) or a group of the formula -CO.$OR^8$ or -CO.NH.$SO_2$.$R^9$ in which $R^8$ is hydrogen or a non-toxic, biodegradable residue of a physiologically acceptable alcohol or phenol, and $R^9$ is (1-6C)alkyl, (3-8C)cycloalkyl or phenyl; and wherein any of said phenyl moieties of $R^1$, $R^2$, $R^3$ or $R^9$ may be unsubstituted or bear one or two substituents independently selected from (1-4C)alkyl, (1-4C)alkoxy, halogeno, cyano and trifluoromethyl; or an N-oxide thereof; or a non-toxic salt thereof.

2. A compound as claimed in claim 1 wherein $R^1$ is hydrogen, methyl, ethyl, propyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl or 2-phenylethyl;
$R^2$ is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, phenyl, benzyl, 1-phenylethyl or 2-phenylethyl;

$R^3$ is selected from hydrogen, methyl, ethyl, propyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl, 2-phenylethyl, fluoro, chloro, bromo, iodo, methoxy, ethoxy, amino, methylamino, ethylamino, butylamino, dimethylamino, diethylamino and dipropylamino;

$R^4$ is a benzoyl group, the phenyl group of which is unsubstituted or bears one or two substituents independently selected from methyl, ethyl, methoxy, ethoxy, chloro, bromo, iodo, cyano, trifluoromethyl, nitro, hydroxy, carboxy, formamido, acetamido, propanamido, formyl, acetyl, butyryl, trifluoromethoxy, 2-fluoroethoxy, 2,2,2-trifluoroethoxy, 3,3,3-trifluoropropoxy, hydroxymethyl, 1-hydroxyethyl, 2-hydroxyethyl, 2-methoxyethyl, 2-ethoxyethyl, carbamoyl, N-methylcarbamoyl, N-ethylcarbamoyl, N,N-dimethylcarbamoyl, N,N-diethylcarbamoyl, sulphamoyl, N-methylsulphamoyl, N-ethylsulphamoyl, N,N-dimethylsulphamoyl, N,N-diethylsulphamoyl, methoxycarbonyl, ethoxycarbonyl, propoxycarbonyl, methanesulphonamido, ethanesulphonamido, methylthio, ethylthio, methylsulphinyl, ethylsulphinyl, methylsulphonyl, ethylsulphonyl, phenyl, phenoxy, benzyloxy, benzyloxycarbonyl, benzamido, benzenesulphonamido, the benzene moiety of the last six groups optionally bearing a fluoro, chloro, bromo, methyl, ethyl, methoxy or ethoxy substituent;

$R^6$ is hydrogen, methyl or ethyl;

$R^7$ is selected from hydrogen, methyl, ethyl, methoxy, ethoxy, fluoro, chloro, bromo, iodo, trifluoromethyl, cyano and nitro;

X is phenylene optionally bearing a substituent selected from methyl, ethyl, methoxy, ethoxy, fluoro, chloro, bromo, iodo, trifluoromethyl, cyano and nitro;

$R^8$ is hydrogen or a residue derived from a (1–6C)alkanol, or phenol or glycerol; and $R^9$ is methyl, ethyl, propyl, isopropyl, butyl, pentyl, cyclobutyl, cyclopentyl, cyclohexyl or phenyl;

and wherein any of said phenyl moieties may be unsubstituted or bear one or two substituents selected from methyl, ethyl, methoxy, ethoxy, fluoro, chloro, bromo, cyano and trifluoromethyl.

3. A compound as claimed in claim 1 wherein X is p-phenylene and Z is 1H-tetrazol-5-yl attached at the ortho position relative to X.

4. A compound of formula Ib

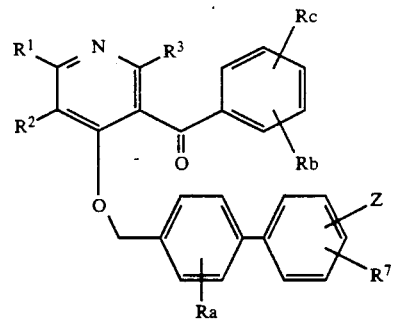

wherein $R^1$, $R^2$, $R^3$, $R^7$ and Z have any of the meanings defined in claim 1, 2 or 3; Ra is hydrogen, (1–4C)alkyl, (1–4C)alkoxy, halogeno, trifluoromethyl, cyano or nitro; and Rb and Rc are independently selected from hydrogen, (1–4C)alkyl, (1–4C)alkoxy, halogeno, cyano, trifluoromethyl, nitro, hydroxy, carboxy, (1–4C)alkanoylamino, (1–4C)alkanoyl, fluoro(1–4C)alkoxy, hydroxy(1–4C)alkyl, (1–4C)alkoxy(1–4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1–4C)alkoxycarbonyl, (1–4C)alkanesulphonamido, (1–4C)alkyl.S(O)$_n$-(in which n is zero, 1 or 2) phenyl, phenoxy, benzyloxy, benzyloxycarbonyl, benzamido and benzenesulphonamido, the benzene moiety of the last six groups optionally bearing a halogeno, (1–4C)alkyl or (1–4C)alkoxy substituent; or a non-toxic salt thereof.

5. A salt as claimed in claim 1 which is selected from the group consisting of salts with acids forming physiologically acceptable anions and, for those compounds of formula I which are acidic, alkali metal, alkaline earth metal, aluminium and ammonium salts, and salts with organic bases affording physiologically acceptable cations.

6. A method for antagonising one or more of the action of angiotensin II in a warm blooded animal requiring such treatment which comprises administering to said animal an antagonistically effective amount of a compound of formula I, or a non-toxic salt thereof, as defined in claim 1.

7. A pharmaceutical composition which comprises a compound of the formula I, or a non-toxic salt thereof, as claimed in claim 1, together with a pharmaceutically acceptable diluent or carrier.

8. A compound of the formula III

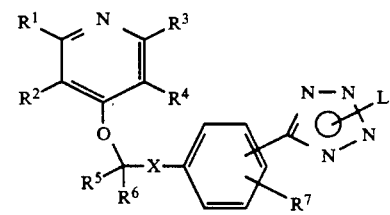

wherein $R^1$, $R^2$, $R^3$, $R^4$, $R^5$, $R^6$ and X have any of the meanings defined in claim 1, and L is a protecting group.

9. A compound as claimed in claim 1 which is:
3-benzoyl-2,6-dimethyl-4-[(2'-(1H-tetrazol-5-yl)biphenyl-4-yl)methoxy]pyridine;
3-benzoyl-6-ethyl-2-methyl-4-[(2'-(1H-tetrazol-5-yl)biphenyl-4-yl)methoxy]pyridine;
or a non-toxic salt thereof.

* * * * *